Figure 1:
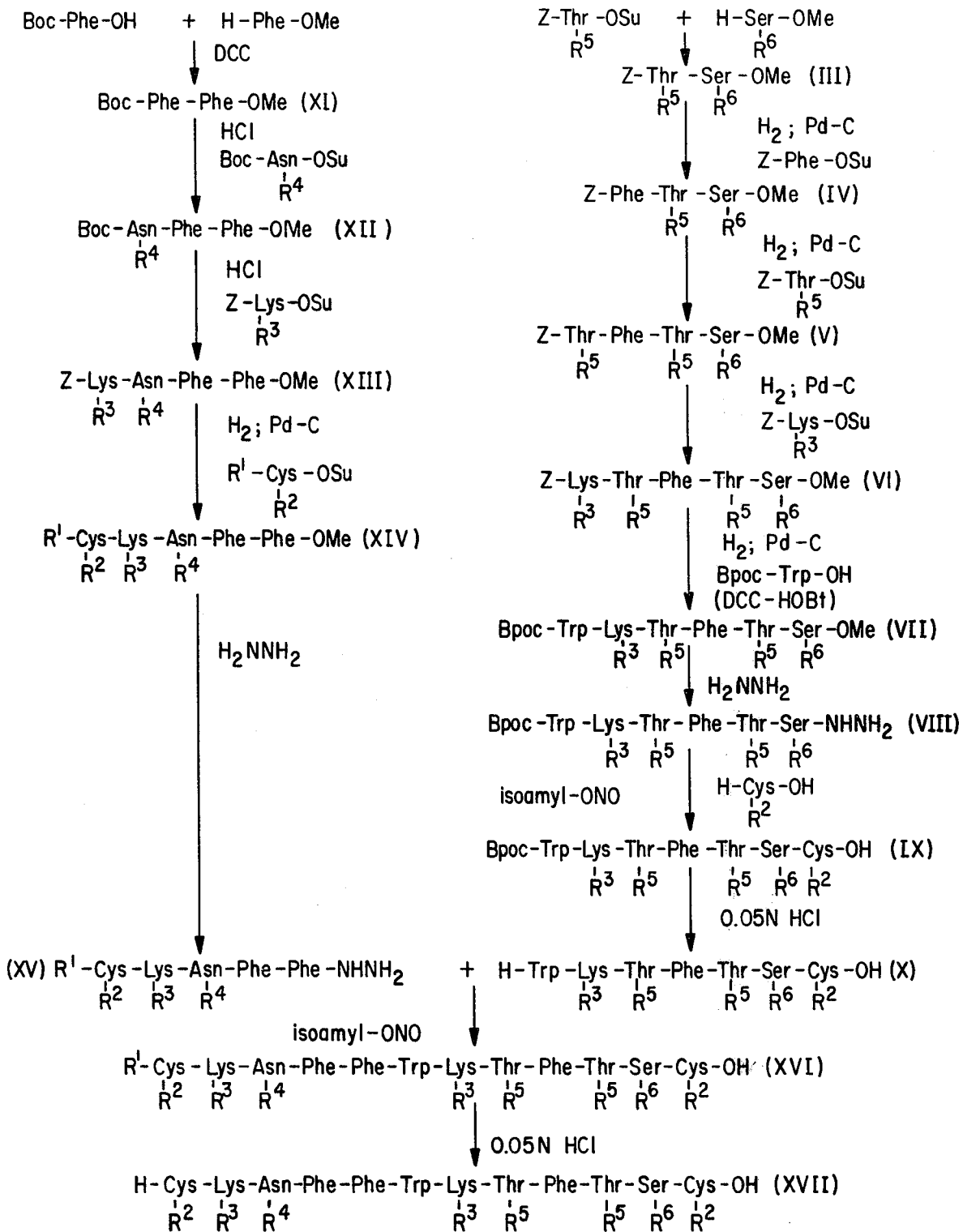

United States Patent [19] [11] 4,145,337
Dairman et al. [45] Mar. 20, 1979

[54] AMINOETHYLGLYCINE CONTAINING POLYPEPTIDES

[75] Inventors: Wallace M. Dairman, Monsey, N.Y.; Arthur M. Felix, West Caldwell, N.J.; Hugo E. Gallo-Torres, Livingston, N.J.; Edgar P. Heimer, Sparata, N.J.; Johannes A. Meienhofer, Upper Montclair, N.J.

[73] Assignee: Hoffmann-La Roche Inc., Nutley, N.J.

[21] Appl. No.: 840,922

[22] Filed: Oct. 11, 1977

[51] Int. Cl.$^2$ .................... C07C 103/52; A61K 37/02
[52] U.S. Cl. ............................. 260/112.5 S; 424/177
[58] Field of Search ................. 260/112.5 S; 424/177

[56] References Cited

U.S. PATENT DOCUMENTS 3,862,925  1/1975  Sarantakis .................... 260/112.5 S Primary Examiner—Delbert R. Phillips
Attorney, Agent, or Firm—Jon S. Saxe; George M. Gould

[57] ABSTRACT

Novel somatostatin analogues containing one or more aminoethylglycyl residues at the amino and/or carboxyl terminus or in the ring position are described. The compounds are potent and long lasting inhibitors of gastric acid secretion.

14 Claims, 2 Drawing Figures

AMINOETHYLGLYCINE CONTAINING POLYPEPTIDES

BACKGROUND OF THE INVENTION

The structure of the growth hormone release inhibiting factor, somatostatin (GH-RIH; SRIF) has been determined by Brazeau et al., Science 179, 77 (1973). Several techniques for synthesizing somatostatin have been reported in the literature, including the solid phase method of Rivier, J. A. C. S., 96, 2986 (1974) and the solution method of Sarantakis et al, Biochem. Biophys. Res. Comm., 54, 234 (1973) and Immer et al., Helv. Chim. Acta., 57, 730 (1974). See also U.S. Pat. No. 3,862,925.

The preparation of somatostatin and acylated des-(Ala[1], Gly[2]) derivatives is described in U.S. Pat. No. 3,904,594.

Bloom et al. Lancet, II, 1106 (1974) have shown that somatostatin inhibits basal gastric secretion and gastrin release. Subcutaneous administration of somatostatin in rats has been shown to have prophylactic effect on restraint ulcer formation (Zierden et al., Res. Exp. Med., 168, 199 (1976). Infusion of somatostatin in man has been reported to stop peptic ulcer bleeding (Rasche et al, Klin, Wschr., 54, 977 (1976). However, the inhibitory effects of somatostatin on gastric secretion (chronic fistula dog) were shown to be of short duration (Torchiana et al, Proc. Soc. Exp. Biol. Med., 154, 449 [1977]). Thus in order to have clinical therapeutic value, new analogs of somatostatin are believed to be required which analogs would have long lasting and specific acitivity. A number of analogs of somatostatin have been prepared and are described in the scientific and patent literature. A summary of such references follows:

(D-Trp[8])-Somatostatin—Rivier et al, Biochem. Biophys. Res. Comm., 65, 746 (1975)
(Ala[3]—Ala[14])-Somatostatin —U.S. Pat. No. 3,842,066
Des (Ala[1], Gly[2], Asn[5])-Somatostatin—U.S. Pat. No. 3,882,098
Derivatives of Somatostatin—U.S. Pat. No. 3,917,581
A cyclic undecapeptide Somatostatin analog—Sarantakis et al., Biochem. Biophys. Res. Comm. 73 336 (1976)
Des(Ala[1]Gly[2])—desamino (Cys[3]) descarboxy(Cys[14]) dicarba[3,14]-Somatostatin—Veber et al., J. A. C. S. 98 2367 (1976)
Cyclic Dodecapeptide Analogs of Somatostatin—U.S. Pat. No. 4,000,259
Des (Ser[13])-Somatostatin—U.S. Pat. No. 3,933,784
(Tyr[3], Tyr[14])—Somatostatin—U.S. Pat. No. 3,988,308
Cyclic Somatostatin Disulfide Analogs—U.S. Pat. No. 3,997,517
(Acyl-D-α-amino acid -Gly-Gly-Tyr-Ala)[1]-Somatostatin—U.S. Pat. No. 3,988,795

References relating to aminoethylglycine may be summarized as follows:

Preparation of aminoethylglycine—U.S. Pat. No. 2,387,725
Use as creatine analog—Rowley et al, J. A. C. S., 93, 5542 (1971)
Incorporation of aminoethylglycine into positions 3,4 of bradykinin—Atherton et al., J. Chem. Soc. C 3393 (1971)
Use of aminoethylglycine in a diagnostic test for malabsorption—U.S. Pat. application Ser. No. 759,221, filed Jan. 13, 1977.

It is further of interest to not that while the (D-Trp[8])-somatostatin analog exhibits higher potency than somatostatin in inhibition of growth hormone, insulin and glucagon, that analog is less potent in inhibition of pentagastrin-induced gastric acid secretion. See for example Brown et al., Science 196, 1467 (1977) at 1468.

DESCRIPTION OF THE INVENTION

The present invention relates to novel anlaogs of somatostatin which contain one or more aminoethylglycine (Aeg) residues at the amino and/or carboxyl-terminals or in the ring position. The compounds of the present invention can be represented by the following formula $$X\text{-Lys-Asn-Phe-Phe-}A\text{-Lys-Thr-Phe-Thr-Ser-}Y \qquad I$$

wherein X independently is selected from H-(Aeg)$_m$-Cys- and H-(Aeg)$_m$-Ala-Gly-Cys-; A is L-Trp or D-Trp; Y independently is -Cys-(Aeg)$_n$-OH; X and Y taken together are an aminoethylglycyl radical in the ring position, m and n are independently selected from 0,1,2,3 and 4 provided that at least one of X or Y contains at least one Aeg radicals, and the cyclic disulfide compounds, the protamine zinc and protamine aluminum complexes and the pharmaceutically acceptable acid addition salts thereon.

Representative compounds of the present invention include the following:

H-Aeg-Cys-Lys-Asn-Phe-Phe-Trp-Lys-Thr-Phe-Thr-Ser-Cys-OH

H-Aeg-Aeg-Cys-Lys-Asn-Phe-Phe-Trp-Lys-Thr-Phe-Thr-Ser-Cys-OH
H-Aeg-Ala-Gly-Cys-Lys-Asn-Phe-Phe-Trp-Lys-Thr-Phe-Thr-Ser-Cys-OH
H-Aeg-Cys-Lys-Asn-Phe-Phe-D-Trp-Lys-Thr-Phe-Thr-Ser-Cys-OH

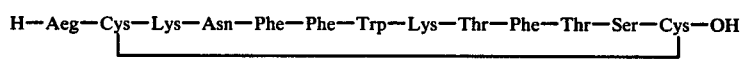

H-Aeg-Aeg-Cys-Lys-Asn-Phe-Phe-D-Trp-Lys-Thr-Phe-Thr-Ser-Cys-OH

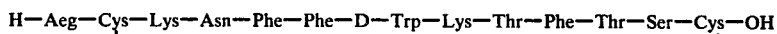

H-Cys-Lys-Asn-Phe-Phe-Trp-Lys-Thr-Phe-Thr-Ser-Cys-Aeg-OH

H-Cys-Lys-Asn-Phe-Phe-D-Trp-Lys-Thr-Phe-Thr-Ser-Cys-Aeg-OH
H-Aeg-Cys-Lys-Asn-Phe-Phe-Trp-Lys-Thr-Phe-Thr-Ser-Cys-Aeg-OH
H-Aeg-Cys-Lys-Asn-Phe-Phe-D-Trp-Lys-Thr-Phe-Thr-Ser-Cys-Aeg-OH may be optionally substituted in the aromatic ring with halo, tert.-butyl and tetrahydropyran-2-yl; and $R^6$ is hydrogen or a conventional protecting group for the hydroxyl group of the serine which is independently selected from the protecting groups set forth for $R^5$ above; is prepared by solution phase synthesis following the strategy outlined in FIG. 1.

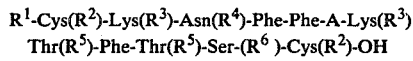

The compounds of the present invention can be conveniently prepared by either solution phase or solid phase peptide synthesis issuing procedures well known in the art. In one preferred process embodiment a key novel intermediate of the formula $R^1$-Cys($R^2$)-Lys($R^3$)-Asn($R^4$)-Phe-Phe-A-Lys($R^3$)
Thr($R^5$)-Phe-Thr($R^5$)-Ser-($R^6$)-Cys($R^2$)-OH     II where A is as above; $R^1$ is hydrogen or a conventional α-amino protecting group selected from benzyloxycarbonyl which may be optionally substituted in the aromatic ring such as by 4-chloro, 2-bromo, 2,4-dichloro, 4-nitro, 4-methoxy, 3,5-dimethoxy, 4-methyl, 2,4,6-trimethyl, 4-phenylazo, 4-(4'-methoxyphenylazo), 2-(N,N-dimethylcarbonamido), 4-dihydroxyboryl, and 2-nitro-4,5-dimethoxy; urethane type protecting groups such as 4-toluenesulfonylethyloxycarbonyl, 9-fluorenylmethyloxycarbonyl and related base cleavable groups, 5-benzisoxazolylmethylene-oxycarbonyl, methylthio and methylsulfonylethyloxycarbonyl, isonicotinyloxycarbonyl, haloethyloxycarbonyl, diisopropylmethyloxycarbonyl, benzhydryloxycarbonyl, isobornyloxycarbonyl, dinitrodiphenylmethyloxycarbonyl, tert.-butyloxycarbonyl, tert.-amyloxycarbonyl, adamantyloxycarbonyl cyclopentyloxycarbonyl, methylcyclobutyloxycarbonyl, methylcyclohexyloxycarbonyl, 2-arylisopropyloxycarbonyl groups such as 2-(p-biphenylyl) isopropyloxycarbonyl, 2-(4-pyridyl)isopropyloxycarbonyl and related nitrogen containing urethane groups; acyl groups, such as formyl, trifluoroacetyl, phthaloyl, benzenesulfonyl, acetoacetyl, chloroacetyl, 2-nitrobenzoyl, 4-toluenesulfonyl; sulfenyl groups such as benzenesulfenyl, o-nitrophenylsulfenyl and related sulfentyl groups; and aryl-lower alkyl groups such as diphenylmethyl and triphenylmethyl;

$R^2$ is a conventional protecting group for the sulfhydryl group independently selected from the group consisting of benzyl; methyl-, methoxy or nitrobenzyl; trityl; benzyloxycarbonyl, benzhydryl, tetrahydropyranyl, carboxymethyl, acetamidomethyl, benzoyl, benzylthiomethyl, ethylcarbamyl, thioethyl, p-methoxybenzyloxycarbonyl, and the sulfonate salt;

$R^3$ is a conventional protecting group for the epsilon amino group of lysine selected from benzyloxycarbonyl; halo- or nitrobenzyloxycarbonyl; tosyl, diisopropylmethoxycarbonyl; t-amyloxycarbonyl and t-butyloxycarbonyl $R^4$ is hydrogen or a conventional protecting group for the carboxamide group selected from xanthenyl; 4,4'-dimethoxyhydryl; 4,4'-dimethylbenzhydryl; benzhydryl and tert.-butyl $R^5$ is hydrogen or a conventional protecting group for the hydroxyl group of threonine selected from benzyl; 2,6dichlorobenzyl; benzyloxycarbonyl which Methods used to couple the intermediate fragments combined in the preparation of the compounds of Formula II include the N-hydroxysuccinimide ester method (Anderson et al, J. Amer. Chem. Soc., 85, 3039 [1963]) the carbodiimidehydroxybenzotriazole method (König and Geiger, Chem. Ber. 103, 788 [1970]); the dicyclohexylcarbodiimide method (Sheehan and Hess, J. Amer. Chem. Soc., 77, 1067 (1955) and the Honzl-Rudinger modified azide coupling method (Honzl and Rudinger. Coll. Czech. Chem. Commun. 26, 2333 (1961)

The compounds of formula II having a free amino terminal ($R^1$=H) are particularly useful for the synthesis of the novel $NH_2$-terminal Aeg-somatostatin analogs of formula I. Such analogs may be conveniently prepared by coupling a compound of formula II with a suitable activated protected aminoethylglycyl containing residue such as, for example, Boc-Aeg(Boc)-OSu, Boc-Aeg(Boc)-Aeg(Boc)OSu or Boc-Aeg(Boc)-Ala-Gly-OSu to give the respective protected final peptides corresponding to formula I. Deprotection is accomplished with trifluoroacetic acid followed by treatment with aqueous mercuric acetate at pH 4. Purification of the resulting peptide products can be readily accomplished by procedures well known in the peptide chemistry art for this purpose such as for example by gel filtration.

In the solution phase process embodiment of the present invention preferred substituent groups include: $R^1$ is hydrogen or 2-(p-biphenylyl) isopropyloxycarbonyl (Boc); $R^2$ is acetamidomethyl (Acm); $R^3$ is t-butyloxycarbonyl (Boc); $R^4$ is hydrogen; $R^5$ is tert.-butyl and $R^6$ is tert.-butyl.

The solid phase method of preparing compounds of formula I of the present invention is generally known in the art and is described by Merrifield, J.A.C.S., 85, 2149 (1963). The resin support employed may be any suitable resin conventionally employed in the art for the solid phase preparation of polypeptides, preferably polystyrene which has been crosslinked with from 0.5 to about 3 percent divinylbenzene, which has been either chloromethylylated or hydroxymethylated to provide sites for ester formation with the initially introduced α-amino and side chain protected amino acid.

An example of a hydroxymethyl resin is described by Bodanszky et al., Chem. Ind. (London) 38, 1597-98 (1966). A chloromethylated resin is commercially available from Bio-Rad Laboratories, Richmond, California and the preparation of such a resin is described by Stewart et al., "Solid Phase Peptide Synthesis" (Freeman & Co., San Francisco 1969), Chapter 1, pp 1-6. The α-amino and sulfhydryl protected cysteine such as $N^\alpha$-t-Boc-S-p-methoxybenzyl-L-cysteine or protected aminoethylglycyl residue such as $N^\alpha$-t-Boc-Aeg($N^\epsilon$-t-Boc)-OH.

The resultant peptide may be removed from the resin support by reaction with HF at 0° for 1 hr in the presence of anisole. Purification can be carried following the same procedures used in the solution phase synthesis, i.e., gel filtration. In the solid phase process embodiment of the present invention preferred protecting groups for side chain substituents include para-methoxybenzyl for cysteine; benzyl for serine; benzyl for threonine; 2-chlorobenzyloxycarbonyl for lysine and tert.-butyloxycarbonyl for aminoethylglycine.

The aforesaid solution and solid phase synthesis produce compounds of formula I which are linear. Conversion to the cyclic form involving formation of the disulfide bridge between the cysteine moieties can be achieved by mildly oxidizing the linear compound preferably with potassium ferricyanide by exposure of the linear compound to atmospheric oxygen.

Figure 2:
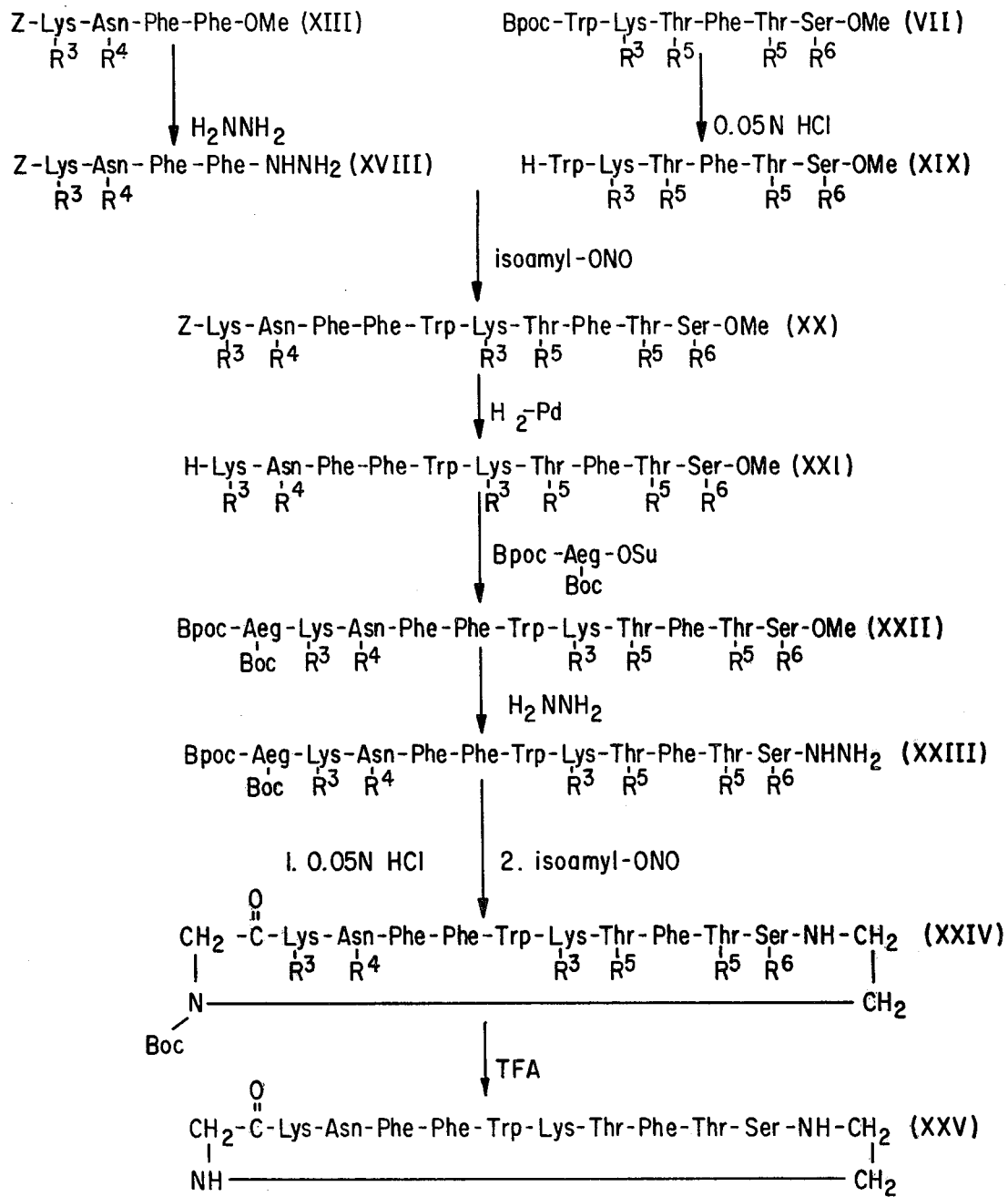

Preparation of the compounds of formula I having an aminoethylglycine radical in the ring position can be conveniently achieved following the solution phase scheme set forth in FIG. 2. Conversion of compound XIII (prepared as an intermediate in accordance with the process of FIG. 1) to the hydrazide XVIII, followed by an azide coupling reaction with compound XIX. The latter compound is derived from compound VII, also an intermediate in the reaction scheme of FIG. 1, by mild acid treatment. The $N^\alpha$-Boc group from the resultant protected decapeptide XX was selectively removed with 0.05 N HCl and the product XXI coupled with Bpoc-Aeg(Boc)-OSu. The protected undecapeptide XXII was converted to the hydrazide XXIII, the $N^\alpha$-Bpoc-group was selectively removed as above and treatment with isoamylnitrite provided the protected product XXIV. Deprotection was accomplished with trifluoroacetic acid to produce the desired cyclic compound XXV.

It should be noted that any of the aforementioned process aspects can be employed in preparing compounds of formula I containing D-Trp by substituting the corresponding protected D-Trp-compound for the L-Trp in the appropriate point in the synthesis. Thus, for example, introduction of Bpoc-D-Trp-OH in the conversion of Compound VI to compound VII in the FIG. 1 scheme will produce the corresponding D-Trp analog of compound XVII.

The compounds of the present invention have valuable pharmacological properties. They are, for example, gastric anti-secretory agents as evidenced by their ability to inhibit the basal gastric acid secretion in the nonanesthetized acute gastric fistula rat.

The compounds of formula I may be combined with various typical pharmaceutical carriers to provide compositions suitable for use in the treatment of gastric and/or duodenal ulcers. The dosage of these compounds is dependent upon various factors, such as the particular compound employed and the extent of the dysfunction being treated. Typical dosages for use as an anti-ulcer agent vary from 0.1 to 100 mg./kg. per day administered parenterally.

Compounds of formula I form pharmaceutically acceptable acid addition salts with a variety of inorganic and organic acids such as sulfuric, phosphoric, hydrochloric, hydrobromic, hydroiodic, nitric, sulfamic, citric, lactic, pyruvic, oxalic, maleic, succinic, tartaric, cinnamic, acetic, trifluoroacetic, benzoic, salicylic, gluconic, ascorbic and related acids.

Abbreviations connote the amino acids defined in accordance with the nomenclature rules published by the IUPAC-IUB Commission on Biochemical Nomenclature in Biochem. J., 126, 773 (1972). The amino acids have the L-stereochemical configuration unless otherwise indicated.

Aminoethylglycine as used herein refers to N-(2-aminoethyl) glycine.

MATERIALS

All amino acid derivatives were of the L-configuration unless otherwise stated. The 1% cross-linked chloromethylated polystyrene-divinylbenzene resin (200–400 mesh; 0.90 mmol Cl/g) was an article of commerce and converted to hydroxymethyl resin by the procedure described in Stewart and Young, Solid Phase Peptide Synthesis, W. H. Freeman ed., p. 27–28 (1969).

METHODS

Amino acid analyses were performed on the Beckman Model 121M Amino Acid Analyzer. The free peptides were hydrolyzed in 6M HCl in sealed, evacuated tubes for 24 hr at 110°. Resin hydrolysates were carried out on silica gel G plates in the following systems: (A) chloroform-methanol-acetic acid (85:10:5) (B) chloroform-methanol-acetic acid (80:2:0.4) (C) n-butanol-acetic acid-pyridine-water (15:3:10:12), (D) n-butanol-0.2 M acetic acid-ethanol-pyridine (upper phase; 4.7:1:1), (E) n-propanol-pyridine-water-acetic acid-ethyl acetate (5:4:6:1:4), (F) chloroform-methanol-acetic acid (70:20:5), (G) chloroform-methanol-acetic acid (85:15:5) and developed with chlorine-tolidine. Melting points were determined on a Reichert hot stage apparatus and are uncorrected. High performance liquid chromatography was carried out on silica gel 60. Optical rotations were measured in a jacketed 1-dm cell on a Perkin-Elmer Model 141 Polarimeter.

One cycle of the solid phase synthesis using the symmetrical anhydride methodology consisted of (a) methylene chloride, three times for 5 min.; (b) 25% trifluoroacetic acid*-methylene chloride 2 min; (c) 25% trifluoroacetic acid*-methylene chloride, 30 min; (d) methylene chloride, three times for 5 min; (e) 5% diisopropylethylamine-methylene chloride, 2 min; (f) 5% diisopropylethylamine-methylene chloride, 10 min; (g) methylene chloride, three times for 5 min; (h) DMF, three times for 5 min; (i) methylene chloride, three times for 5 min; (j) premix Boc-amino acid (6 eq) with DCC (3 eq) for 15 min at 0°; 15 min at 25°, filter and couple for 15 min followed by (k) 0.4 M diisopropylethylamine in methylene chloride (3 eq) for 15 min; (l) methylene chloride, three times for 5 min; (m) DMF, three times for 5 min; (n) absolute ethanol, three times for 5 min; (o) methylene chloride, three times for 5 min; (p) diisopropylethylamine (1 eq) in methylene chloride, 2 min followed by (q) fluorescamine (1 eq) in methylene chloride, 15 min; (r) methylene chloride, three times for 5 min; (s) absolute ethanol, three times for 5 min; (t) methylene chloride, three times for 5 min.

\* 1% 1,2-ethanedithiol was added to the TFA solution for the deprotection of the Boc-Trp-residue.

EXAMPLE 1

N-Benzyloxycarbonyl-O-t-butyl-L-threonine O-t-butyl-L-serine methyl ester

A solution of N-benzyloxycarbonyl-O-butyl-L-threonine N-hydroxysuccinimide ester (101.61 g., 0.250 mole) and O-t-butyl-L-serine methyl ester HCl (53.00 g., 0.250 mole) in DMF (500 ml) was cooled to 0° and treated with triethylamine (35.0 ml.; 0.25 mole). Stirring proceeded at 0° for 1 hour and 25° for 16 hours. It was evaporated to dryness, taken up in ethyl acetate (300 ml.), extracted in turn with 10% NaHCO$_3$ (3 × 200 ml.), saturated NaCl (3 × 200 ml.), 1 M citric acid (3 × 200 ml.), saturated NaCl (3 × 200 ml.), dried over MgSO$_4$, filtered and evaporated to a clear colorless oil (112.4 g.; 96.5%); $[\alpha]_D^{25}$ + 30.34° (C, 1 MeOH); R$_f$ 0.90 (A); 0.94(B); 0.76(D). Anal. Calcd for C$_{24}$H$_{38}$N$_2$O$_7$: C, 61.78; H, 8.21; N, 6.00. Found: C, 61.62; H, 8.27; N, 5.86.

EXAMPLE 2

N-Benzyloxycarbonyl-L-phenylalanyl-O-t-butyl-L-threonyl-O-t-butyl-L-serine methyl ester A solution of the protected dipeptide of Example 1 (90.8 g., 0.194 mole), in methanol (600 ml.) containing 5% Pd on BaSO$_4$ (25 g.) and 2 ml. of glacial acetic acid was hydrogenated at atmospheric pressure using a stream of prepurified hydrogen (dried over conc. H$_2$SO$_4$) for a period of 3 hours in a Vibro-Mixer apparatus. The reaction mixture was filtered through a pad of Celite, evaporated to dryness and reevaporated three times from benzene. The resultant oil was taken up in DMF (750 ml.), cooled to 0° and reacted with N-benzyloxycarbonyl-L-phenylalanine N-hydroxysuccinimide ester (77.0 g., 0.194 mole). Workup proceeded as described above for Example 1 to give 119 g. (96.8%) of white amorphous product; $[\alpha]_D^{25}$ 11.22° (C, 1 DMF); R$_f$ 0.70 (B). Anal. calcd for C$_{33}$H$_{47}$N$_3$O$_8$·½H$_2$O: C, 63.66; H, 7.77; N, 6.75. Found: C, 63.70; H, 8.02; N, 674.

EXAMPLE 3

N-Benzyloxycarbonyl-O-t-butyl-L-threonyl-L-phenylalanyl-O-t-butyl-L-threonyl-O-t-butyl-L-serine methyl ester A solution of the protected tripeptide of Example 2 (11.2 g., 0.018 mole) in methanol (250 ml.) containing 5% Pd on BaSO$_4$ (6.75 g.) and 1 ml. of glacial acetic acid was hydrogenated as described above for the preparation of the product of Example 2 and evaporated to dryness. The resultant oil was taken up in DMF (70 ml.), cooled to 0° and coupled with N-benzyloxycarbonyl-O-t-butyl-L-threonine N-hydroxysuccinimide ester (7.32 g., 0.018 mole). Workup as described for Example 1 was followed by chromatography on Sephadex LH 20 using 95% ethanol as eluant. Crystallization from ether-gexane gave 12.9 g. (9.8%) of white amorphous product; m.p. 113.5°–115°; $[\alpha]_D^{25}$ + 23.63° (C, 1 DMF); R$_f$ 0.75 (B). Anal. calcd for C$_{41}$H$_{62}$N$_4$O$_{10}$: C, 63.87; H, 8.11; N, 7.27. Found: C, 63.99; H, 8.18; N, 7.21.

EXAMPLE 4

N$^\alpha$-Benzyloxycarbonyl-N$\epsilon$-t-butyloxycarbonyl-L-lysyl-O-t-butyl-L-threonyl-L-phenylalanyl-O-t-butyl-L-threonyl-O-t-butyl-L-serine methyl ester The protected tetrapeptide of Example 3 (123.6 g., 0.160 mole), in methanol (650 ml.) containing 5% Pd on BaSO$_4$ (25 g.) and 2 ml. of glacial acetic acid was hydrogenated as described above for Example 2 and evaporated to dryness. The resultant oil was taken up in DMF (375 ml.), cooled to 0° and coupled with N$^\alpha$-benzyloxycarbonyl-N$^\epsilon$-t-butyloxycarbonyl-L-lysine N-hydroxysuccinimide ester (76.4 g., 0.160 mole). Workup as described for Example 1 was followed by high performance liquid chromatography on silica gel 60 (8.25 × 80 cm column) using an ethanolchloroform gradient. Crystallization from ether-petroleum ether gave 152.6 g. (95.4%) of white amorphous product, m.p. 87°–88°; $[\alpha]_D^{25}$ +18.19° (C 1, DMF); R$_f$ 0.54 (B). Anal. calcd for C$_{52}$H$_{82}$N$_6$O$_{13}$: C, 62.50; H, 8.27; N, 8.41. Found: C, 62.43; H, 8.33; N, 8.12.

EXAMPLE 5

N-[2-(p-Biphenylyl)-2-propyloxycarbonyl]-L-tryptophyl-N$^\epsilon$-t-butyloxycarbonyl-L-lysyl-O-t-butyl-L-threonyl-L-phenylalanyl-O-t-butyl-L-threonyl-O-t-butyl-L-serine methyl ester The protected pentapeptide of Example 4 (133.8 g., 0.134 mole), in methanol (650 ml.) containing 5% Pd on BaSO$_4$ (25 g.) and 2 ml. of glacial acetic acid was hydrogenated as described above for Example 2 and evaporated to dryness. The resultant oil was taken up in DMF (600 ml.), cooled to 0° and reacted with N-[2-(p-biphenylyl)-2-propyloxycarbonyl]-L-tryptophan (59.3 g., 0.134 mole) followed by the addition of hydroxybenzotriazole hydrate (24.66 g., 0.161 mole) and dicyclohexylcarbodiimide (27.65 g., 0.134 mole). Stirring proceeded at 0° for 1 hour and 25° for 16 hours. The reaction mixture was filtered and the filtrate evaporated to dryness and purified by high performance liquid chromatography on silica gel 60 (8.25 × 80 cm column) using 1-chlorobutane as eluant. Crystallization from ethyl acetate-petroleum ether gave 146.4 g. (84.7%) of white crystalline product, m.p. 111°–115°; $[\alpha]_D^{25}$ +5.21° (C, 1 DMF); R$_f$ 0.93 (A). Anal. calcd for C$_{71}$H$_{100}$N$_8$O$_{14}$: C, 66.13; H, 7.82; N, 8.69. Found: C, 65.64; H, 8.09; N, 8.43.

EXAMPLE 6

N-[2-(p-Biphenylyl)-2-propyloxycarbonyl]-L-tryptophyl-N$^\epsilon$-t-butyloxycarbonyl-L-lysyl-O-t-butyl-L-threonyl-L-phenylalanyl-O-t-butyl-L-threonyl-O-t-butyl-L-serine hydrazide The protected hexapeptide methyl ester of Example 5 (8.19 g, 6.35 mmole), in 120 ml of n-butanol-DMF (1:1) was treated with hydrazine hydrate (30.7 ml, 0.635 mole, 120 eq) and stirred at 25° for 16 hrs. The reaction mixture was evaporated to dryness and crystallized from methanol-water to give 7.22 g (88.2%) of white granular solid, mp 176°–178°; $[\alpha]_D^{25}$ + 20.32° (C, 1 CHCl$_3$); R$_f$ 0.72 (A). Anal. calcd for C$_{70}$H$_{100}$N$_{10}$O$_{13}$·H$_2$O: C, 64.29; H, 7.86; N, 10.71. Found: C, 64.01; H, 7.77; N, 10.88.

EXAMPLE 7

N-[2-(p-Biphenylyl)-2-propyloxycarbonyl]-L-tryptophyl-N$^\epsilon$-t-butyloxycarbonyl-L-lysyl-O-t-butyl-L-threonyl-L-phenylalanyl-O-t-butyl-L-threonyl-O-t-butyl-L-seryl-S-acetamidomethyl-L-cysteine The protected hexapeptide hydrazide of Example 6 (7.223 g, 5.60 mmole), in DMF (29 ml) was cooled to −20°, and treated with 3.06 M HCl in THF (10.98 ml, 33.6 mmole, 6 eq) followed by isoamylnitrite (1.13 ml, 8.40 mmole, 1.5 eq). Stirring proceeded for 30 min at −20°, cooled to −25° and triethylamine (4.70 ml, 33.6 mmole, 6 eq) added. The temperature was readjusted to −20° and S-acetamidomethyl-L-cysteine hydrochloride (2.561 g, 11.2 mmole, 2.0 eq) added followed by triethylamine (3.14 ml, 22.4 mmole, 4 eq). The pH was maintained at 8.0 by dropwise addition of triethylamine and stirring proceeded at −20° for 1 hr, 2° for 16 hr and 25° for 5 ½ hr. The reaction mixture was evaporated to dryness and the residue was triturated with water and purified by high performance liquid chromatography on silica gel 60 using a methanol-chloroform gradient.

Crystallization from isopropanol-petroleum ether gave 6.07 g (74.8%) of white amorphous solid, mp 18.5°–187.5°; $[\alpha]_D^{25}$ − 8.18° (C, 1 MeOH); $R_f$ 0.59(A). Anal. calcd for $C_{76}H_{108}N_{10}O_{16}S$: C, 62.96; H, 7.51; N, 9.66; S, 2.21. Found: C, 62.32; H, 7.59; N, 9.88; S, 2.35.

EXAMPLE 8

L-trytophyl-Nε-t-butyloxycarbonyl-L-lysyl-O-t-butyl-L-threonyl-L-phenylalanyl-O-t-butyl-L-seryl-S-acetamidomethyl-L-cysteine The protected heptapeptide from Example 7 (5.558 g, 3.83 mmole) was dissolved in 0.05 M HCl in DMF (364 ml, 18.2 mmole, 4.75 eq) containing anisole (20.9 ml) and mercaptoethanol (3.42 ml). Stirring proceeded for 1 hr at 25°, evaporated to dryness, triturated with ether and crystallized from methanol-water. White amorphous solid (3.487 g, 75.2%) was obtained, mp 200°–202°, $[\alpha]_D^{25}$ + 14.63° (C 0.5, MeOH; $R_f$ 0.72(C). Anal. calcd for $C_{60}H_{94}N_{10}O_{14}S \cdot H_2O$: C, 58.61; H, 7.87; N, 11.39; S, 2.61. Found: C, 58.62; H, 7.79; N, 11.01; S, 2.53.

EXAMPLE 9

N-t-Butyloxycarbonyl-L-phenylalanyl-L-phenylalanine methyl ether

A solution of N-t-butyloxycarbonyl-L-phenylalanine (34.5 g, 0.13 mole) in $CH_2Cl_2$ (400 ml) was cooled to 0° and L-phenylalanine methyl ester hydrochloride (28.0 g, 0.13 mole) added followed by dicyclohexylcarbodiimide (29.5 g, 0.143 mole) and triethylamine (13.2 g, 0.13 mole) and stirred at 0° for 2 hr and 25° for 16 hr. The reaction mixture was filtered, evaporated to dryness, taken up in ethyl acetate and extracted with water. It was dried ($Na_2SO_4$), filtered, evaporated and crystallized from ethyl acetate-petroleum ether. Recrystallization from $CH_2Cl_2$-petroleum ether gave 71.73 g (64.7%) of white crystalline product, mp 133–135; $R_f$ 0.91(A).

EXAMPLE 10

N-t-Butyloxycarbonyl-L-asparaginyl-L-phenylalanyl-L-phenylalanine methyl ester

A solution of the protected dipeptide from Example 9 (59.0 g, 0.138 mole) in 3.6 N HCl in THF (3 l) stood for 1.5 hr at 25° and evaporated to dryness and crystallized from THF-ether to give 49.8 g (99.4%) of HCl·H-Phe-Phe-OMe, mp 199°–200°; $[\alpha]_D^{25}$ + 63.5° (C, 1 MeOH). Anal. calcd for $C_{19}H_{22}N_2O_3 \cdot HCl$: C, 62.89; H, 6.39; N, 7.72. Found: C, 62.79; H, 6.41; N, 7.67. This salt was dissolved in DMF (450 ml), cooled to 5°, neutralized with triethylamine (13.9 g, 0.137 mole), coupled with N-t-butyloxycarbonyl-L-asparagine N-hydroxysuccinimide ester (49.86 g, 0.151 mole, 1.1 eq) and stirred at 5° for 1 hr and 25° for 19 hr. The reaction mixture was filtered, evaporated, triturated with water, methanol, ether and crystallized from methanol to give 50.6 g (68.2%) of white solid, mp 192°–194°; $R_f$ 0.63(A).

EXAMPLE 11

N-α-Benzyloxycarbonyl-N^ε-t-butyloxycarbonyl-L-lysyl-L-asparaginyl-L-phenylalanyl-L-phenylalaine methyl ester The protected tripeptide from Example 10 (26.9 g, 0.0498 mole) was deprotected with 3.86 M HCl in THF (1.5 l) as described in Example 10. Crystallization from MeOH-ether gave white crystalline product, mp 191°–193°; $[\alpha]_D^{25}$ + 9.43° (C, 1 MeOH). Anal. calcd for $C_{23}H_{29}N_4O_5 \cdot HCl$: C, 57.92; H, 6.13; N, 11.75. Found: C, 57.39; H, 6.07; N, 11.37. A 21.5 g (0.045 mole) portion of this salt was dissolved in DMF (270 ml), treated with N-α-benzyloxycarbonyl-N-ε-t-butyloxycarbonyl-L-lysine N-hydroxysuccinimide ester (21.56 g, 0.045 mole) and triethylamine (4.55 g, 0.045 mole) and reacted at 0° for 1 hr and 25° for 20 hr. The reaction mixture was worked up as described in Example 10 and crystallized from methanol to give 24.2 g (67.0%) of white crystalline product, mp 208°–210°; $[\alpha]_D^{25}$ −28.92° (C, 0.6 DMF); $R_f$ 0.65(A). Anal. calcd for $C_{42}H_{54}N_6O_{10}$: C, 62.83; H, 6.78; N, 10.47. Found: C, 62.64; H, 6.75; N, 10.40.

EXAMPLE 12

N-[2-(p-Biphenylyl)-2-propyloxycarbonyl]-S-acetamidomethyl-L-cysteinyl-N-ε-t-butyloxycarbonyl-L-lysyl-L-asparaginyl-L-phenylalanyl-L-phenylalanine methyl ester A solution of the protected tetrapeptide of Example 11 (5.00 g 6.23 mmole), in DMF (150 ml) containing 3.1 g of 5% Pd on $BaSO_4$ and 0.5 ml of glacial acetic acid was hydrogenated as described above in Example 2 and evaorated to dryness. The resultant oil was taken up in DMF (85 ml), cooled to 0° and coupled with N-[2-(biphenylyl)-2-propyloxycarboxyl]-S-acetamidomethyl-L-cysteine N-hydroxysuccinimide ester (3.287 g. 6.23 mmol). Reaction proceeded at 0° for 1 hr and 25° for 16 hr. It was evaporated to dryness, triturated with water and crystallized from methanol-ether to give 4.41 g (65.4%) of white crystalline product, mp 180–180.5° d; $[\epsilon]_D^{25}$ -33.34° (C, 1, DMF) $R_f$ 0.70 (A); 0.86 (C); 0.84(E). Anal. calcd for $C_{56}H_{72}N_8O_{12}S$; C, 62.20; H, 6.71; N, 10.36; S, 2.96. Found C, 61.86 H, 6.60 N, 10.36; 2.89.

EXAMPLE 13

N-[2-(p-Biphenylyl)-2-propyloxycarbonyl]-S-acetamidomethyl-L-cysteinyl-N-ε-t-butyloxycarbonyl-L-lysyl-L-asparaginyl-L-phenylalanyl-L-phenylalanine hydrazide The protected pentapeptide methyl ester of Example 12 (3.745 g 3.46 mmole) in 60 ml of n-butanol-DMF (1:1) was treated with hydrazine hydrate (16.7 ml 0.346 mole, 100 eg) and worked up as described in Example 6. Crystallization from DMF-isopropanol gave 3.48 g (93.1%) of amorphous solid, mp 216.5-218.5° ; $[\alpha]_D^{25}$ −42.30° (C, 1 DMF); $R_f$ 0.42 (A) Anal. calcd for $C_{55}H_{72}N_{10}O_{11}S \cdot H_2O$; C, 60.09; H, 6.79; N, 12.74; S, 2.92. Found C, 59.63; H, 6.70; N, 12.98; S, 3.24

EXAMPLE 14

N-[2-(p-Biphenylyl)-2-propyloxycarbonyl]-S-acetamidomethyl-L-cysteinyl-N-ε-t-butyloxcarbonyl-L-lysyl-L-asparaginyl-L-phenylalanyl-L-phenylalanyl-L-tryptophyl-N-ε-t-butyloxycarbonyl-L-lysyl-O-t-butyl-L-threonyl-L-phenylalanyl-O-t-butyl-L-threonyl-O-t-butyl-L-seryl-S-acetamidomethyl-L-cysteine The protected pentapeptide hydrazide, of Example 13 (2.534 g, 2.343 mmole) in DMF (15 ml) was cooled to −20° and treated with 2.90 M HCl in THF (4.85 ml, 14.06 mmole, 6 eq) followed by isoamylnitrite (0.46 ml, 3,397 mmole, 1.45 eq). Stirring proceeded for 30 min at −20°, cooled to −25°, and triethylamine (1.97 ml, 14.06 mmole, 6 eq) added. The temperature was readjusted to −20° and the heptapeptide of Example 8 (3.122 g, 2.577 mmole, 1.1 eq) added followed by triethylamine (0.2361 ml, 2.577 mmole, 1.1 eq). The pH was maintained at 8.0 by dropwise addition of triethylamine and stirring and workup proceeded as described in Example 7. Crystallization from DMF-water gave 4.811 g (90.8%) of off-white amorphous solid, $[\alpha]_D^{25}$ −14.40° (C, 1DMF); $R_f$ 0.27 (A). Anal. calcd for $C_{115}H_{162}N_{18}O_{25}S_2 \cdot H_2O$; C, 60.61; H, 7.25; N, 11.06; S, 2.81. Found: C, 60.40 ; H, 7.36 ; N, 11.03; S, 2.81.

EXAMPLE 15

S-Acetamidomethyl-L-cysteinyl-ϵ-t-butyloxycarbonyl-L-lysyl-L-asparaginyl-L-phenylalanyl-L-phenylalanyl-L-trytophyl-N-ϵ-t-butyloxycarbonyl-L-lysyl-O-t-butyl-L-threonyl-L-phenylalanyl-O-t-butyl-L-threonyl-O-t-butyl-L-seryl-S-acetamidomethyl-L-cysteine The protected dodecapeptide of Example 14 (4.700 g, 2.079 mmole( was dissolved in 200 ml of 0.05 M HCl in DMF (10.0 mmole, 4.81 eq) containing anisole (11.3 ml) and mercaptoethanol (1.9 ml.) Reaction and workup proceeded as described in Example 8Crystallization from DMF-water gave a quantitative yield (4.21 g) of crystalline product, mp 210° dec; $[\alpha]_D^{25}$ −3.00° (C, 1 DMF) $R_f$ 01.21 (F). Anal. calcd for $C_{99}H_{148}N_{18}O_{23}S_2$; C, 58.79; H, 7.38; N, 12.47; S, 3.17. Found C, 58.63 H, 7,74 N, 12.27 S, 3.45 Amino Acid Anal; Lys, 2.06; Asp. 1.04 ; Thr. 1.90 ; Ser, 0.96; Phe, 3.02.

EXAMPLE 16

N-t-Butyloxycarbonyl-N'-(2-t-butyloxycarbonylaminoethyl)glycyl-S-acetamidomethyl-L-cysteinyl-N-ϵ-t-butyloxcarbonyl-L-lysyl-L-asparaginyl-L-phenylalanyl-L-phenylalanyl-L-tryptophyl-N-ϵ-butyloxycarbonyl-L-lysyl-O-t-butyl-L-threonyl-L-phenylananyl-O-t-butyl-L-threonyl-O-t-butyl-L-seryl-S-acetamidomethyl-L-cysteine A solution of the dodecapeptide of Example 15 (750 mg, 0.371 mmole), in DMF (5 ml) at 0° was reacted with N-t-butyloxycarbonyl-N-(2-t-butyloxycarbonylaminoethyl)glycine-N-hydroxysuccinimide ester, (770 mg. 1.854 mmole, 5 eq). N-Methylmorpholine (2.04 ml, 0.381 mmole) was added, the pH maintained at 8.0 and the reaction was continued at 0° for 1 hr. and 25° for 16 hr. The solution was evaporated to dryness. Purification by high performance liquid chromatography (methanolchloroform gradient) and precipitation from DMF-water gave 231 mg (26.8%) of white solid, mp 215° d; $[\alpha]_D^{25}$ −29.74° (C, 0.77 DMF); $R_f$ 0.72 (G). Anal. calcd. for $C_{113}H_{172}N_{20}O_{28}S_2$; C, 58.43; H, 7.46; N, 12.06; S, 2.76. Found C, 58.02; H, 7.70 ; N, 11.40. S, 2.79.

EXAMPLE 17

N-t-Butyloxycarbonyl-N-(2t-butyloxycarbonylaminoethyl)glycyl-N-(2-t-butyloxycarbonylaminoethyl)glycyl-S-acetamidomethyl-L-cysteinyl-N-ϵ-t-butyloxycarbonyl-L-lysyl-L-asparaginyl-L-phenylalanyl-L-phenylalanyl-L-tryptophyl-N-ϵ-t-butyloxycarbonyl-L-lysyl-O-t-butyl-L-threonyl-L-phenylalanyl-O-t-butyl-L-threonyl-O-t-butyl-L-seryl-S-acetamidomethyl-L-cysteine A solution of the dodecapeptide of Example 15 (200 mg, 0.099 mmole), was coupled with N-t-butyloxycarbonyl-N-(2-t-butyloxycarbonylamino ethyl) glycycl-N-2-(t-butyloxycarbonylaminoethyl)glycine N-hydroxysuccinimide ester, (305 mg, 0.495 mmole, 5 eq) in DMF (4 ml) at 0° as described in Example 16 above. Purification by high performance liquid chromatography (methanolchloroform gradient) was followed by precipitation from DMF-water to give 164 mg (65.6%) of white solid $[\alpha]_D^{25}$ −17.64° (C, 1 DMF); $R_f$ 0.49 (G). Anal. calcd for $C_{122}H_{188}N_{22}O_{31}S_2 \cdot H_2O$: C, 57.66; H, 7.54; N, 12.13; S, 2.52. Found C, 57.80; H, 7.11 ; N, 11.50; S, 2.50.

EXAMPLE 18

N-t-Butyloxycarbonyl-N-(2-t-butyloxycarbonylaminoethyl)glycyl-L-alanyl-glycyl-S-acetamidomethyl-L-cysteinyl-N-ξ-t-butyloxy-carbonyl-L-lysyl-L-asparaginyl-L-phenylalanyl-L-phenylalanyl-L-tryptophyl-N-ξ-t-butyloxycarbonyl-L-lysyl-O-t-butyl-L-threonyl-L-phenylalanyl-O-t-butyl-L-threonyl-O-t-butyl-L-seryl-S-acetamido-methyl-L-cysteine A solution of the dodecapeptide of Example 15 (164 mg, 0.081 mmole), was coupled with N-t-butyloxycarbonyl-N-(2-t-butyloxycarbonylamino ethyl)glycyl-L-alanyl-glycine N-hydroxysuccinimide ester, (221 mg, 0.407 mmole, 5 eq) in DMF (2 ml) at 0° as described in Example 16 above. Purification by high performane liquid chromatography (methanol-chloroform gradient) was followed by precipitation from DMF-water to give 208 mg (37.0%) of white solid; $R_f$0.39(G). Anal. calcd for $C_{123}H_{189}N_{23}O_{32}S_2$:C,57.57; H, 7.42; N, 12.55; S, 2.50. Found: C, 57.22; H, 7.24; N, 12.01; S. 2.27.

EXAMPLE 19

Aminoethylglycyl-L-cysteinyl-L-lysyl-L-asparaginyl-L-phenyl-alanyl-L-phenylalanyl-L-tryptophyl-L-lysyl-L-threonyl-L-phenyl-alanyl-L-threonyl-L-seryl-L-cysteine The protected peptide of Example 16 (100 mg, 0.043 mmole), was reacted with trifluoroacetic acid (10 ml) under $N_2$ at 25° for 2 hr, evaporated to dryness, re-evaporated several times from $CH_2Cl_2$, and the residue was taken up in water and adjusted to pH 4.0 (using 0.1 M $NH_4OH$). Mercuric acetate (54.8 mg, 0.172 mmole) was added and stirring proceeded at 25° for 1.5 hr. A gentle stream of $H_2S$ was passsed through the reaction mixture for 15 min filtered and lyophilized. Gel filtration on a 2.5 × 93 cm column of Sephadex G-25 using 2.0N acetic acid-0.01M β-mercaptoethanol as eluant gave a major symmetrical peak. Fractions 61–68 (275–306 ml) were lyophilized to give 29 mg (41.9%) of white amorphous powder; $R_f$ 0.58 (C). Amino acid anal: Lys. 2.12; Asp. 1.08; Phe, 2.98; Thr, 2.04; Ser, 0.91; Aer, 0.88.

EXAMPLE 20

Aminoethylglycyl-aminoethylglycyl-L-cysteinyl-L-lysyl-L-asparaginyl-L-phenylalanyl-L-phenylalanyl-L-tryptophyl-L-lysyl-L-threonyl-L-pehnylalanyl-L-threonyl-L-seryl-L-cysteine The protected peptide of Example 17 (60.6 mg, 0.024 mmole) was reacted with trifluoroacetic acid (10 ml) as described in Example 19 above followed by treatment with mercuric acetate (30.6 mg, 0.096 mmole). Workup proceeded as described in Example 19 and product was purified by gel filtration on a 2.5 × 93 cm column of Sephadex G-25. Fractions 54–67 (243–302 ml) were lyophilized to give 15 mg (36.5%) of white amorphous powder; $R_f$0.56(C); 0.72(E). Amino acid anal: Lys, 2.11; Asp. 1.03; Phe, 3.19; Thr, 2.06; Ser, 0.86; Aeg, 1.74.

EXAMPLE 21

Aminoethylglycyl-L-alanyl-glycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine The protected peptide from Example 18 (52 mg, 0.020 mmole) was reacted with trifluoroacetic acid (10 ml) as described in Example 19 above followed by treatment with mercuric acetate (25.5 mg, 0.080 mmole). Workup proceeded as described in Example 19 and the product was purified by gel filtration on a 2.5 × 93 cm Sephadex G-25 column. Fractions 55–67 (248–302 ml) were lyophilized and rechromatographed on a 0.9 × 54 cm Sephadex G-25 column. Fractions 9–12 (18–24 ml) were lyophilized to give 14.5 mg (41.7%) of white amorphous powder; $R_f$ 0.57(C); 0.76(E); 0.32(D). Amino acid anal: Ala, 0.94; Gly, 1.15; Lys, 2.18; Asp. 1.06; Phe, 3.14; Thr, 2.13; Ser. 0.92; Aeg. 0.81.

EXAMPLE 22

Aminoethylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine (Oxidized form)

The reduced form of the peptide from Example 19 (11.0 mg., 6.8 μmole), was dissolved in 0.62 ml. of 25% acetic acid and treated with potassium ferricyanide until a stable pale yellow color was observed. After standing at 25° for 10 minutes, the pH was adjusted to 5.0 with glacial acetic acid, and stirred with Bio-Rad AG3-X4A for 15 minutes. The mixture was filtered through a fine sintered funnel and the filtrate applied successively onto two columns: Bio-Rad AG3-X4A (chloride form; 3 ml.) and Bio-Rex 70 (chloride form; 3 ml.). The resin in the sintered funnel was rinsed with water (5 ml.) and applied onto the columns as a wash. The Bio-Rex 70 column (0.8 × 12 cm.) was washed with 5% acetic acid (50 ml.) and the peptide displaced with 50% acetic acid. Fractions 1–8 (0–18 ml.) were lyophilized and purified by gel filtration on a 0.9 × 54 cm Sephadex G-25 column. Fractions 10–16 (20–32 ml.) gave a white powder 6.3 mg. (57.8%); $R_f$ 0.57 (C); 0.67 (E); 0.25 (D). Complete disappearance of free sulfhydryls was confirmed by monitoring with Ellman's reagent (see Ellman, Arch. Biochem. Biophys., 82, 70 [1959]).

EXAMPLE 23

N$^\alpha$-Benzyloxycarbonyl-N-$\epsilon$-t-butyloxycarbonyl-L-lysyl-L-asparaginyl-L-phenylalanyl-L-phenylalanine hydrazine The protected tetrapeptide methyl ester of Example II (4.019 g., 5.0 mmole), in 50 ml. of n-butanol-DMF (1:1) was reacted with hydrazine hydrate (26 ml., 0.539 mmole, 108 eq) and stirred at 25° for 22 hours. The reaction mixture was evaporated to dryness and crystallized from DMF-isopropanol to give 3.551 g. (88%) of white amorphous solid, m.p. 233–234.5°; $[\alpha]_D^{25}$ −40.20° (C, 1 DMF); $R_f$ 0.85 (G); 0.82 (C). Anal. calcd for $C_{41}H_{54}N_8O_0$: C, 61.33; H, 6.78; N, 13.96. Found: C, 61.55; H, 6.64; N, 14.14.

EXAMPLE 24

L-Tryptophyl-N-$\epsilon$-t-butyloxycarbonyl-L-lysyl-O-t-butyl-L-threonyl-L-phenylalanyl-O-t-butyl-L-threonyl-O-t-butyl-L-serine methyl ester·HCl The protected hexapeptide of Example 5 (1.935 g, 1.50 mmole), was dissolved in 0.053 M HCl in DMF (134 ml, 7.12 mmole, 4.75 eq) containing anisole (8.19 ml) and mercaptoethanol (1.25 ml). Stirring proceeded for 1 hr at 25°, evaporated to dryness, triturated with ether and petroleum ether to give 1.514 g (89.8%) of off-white amorphous solid; mp 155–159°; $[\alpha]_D^{25}$ +15.15° (C, 1 MeOH); $R_f$ 0.27 (4% MeOH—CHCl$_3$). Anal. calcd for $C_{55}H_{86}N_8O_{12}$·HCl; C, 60.73; H, 8.06; N, 10.30. Found: C, 60.57; H, 8.04; N, 10.12.

EXAMPLE 25

N-$\alpha$-Benzyloxycarbonyl-N-$\epsilon$-t-butyloxycarbonyl-L-lysyl-L-asparaginyl-L-phenylalanyl-L-phenylalanyl-L-tryptophyl-N-$\epsilon$-t-butyloxycarbonyl-L-lysyl-O-t-butyl-L-threonyl-L-phenylalanyl-O-t-butyl-L-threonyl-O-t-butyl-L-serine methyl ester The protected tetrapeptide hydrazide of Example 23 (1.457 g, 1.816 mmole) in DMF (28 ml) was cooled to −20°, and treated with 1.455 M HCl in THF (7.50 ml, 10.9 mmole, 6 eq) followed by isoamylnitrite (0.747 ml, 52.5 mmole, 2.9 eq). Stirring proceeded for 30 min at −20°, cooled to −25° and triethylamine (1.51 ml, 1.087 mmole, 6 eq) added. The temperature was readjusted to −20° and the hexapeptide of Example 24 (2.242 g, 1.998 mmole, 1.1 eq), added followed by triethylamine (0.462 ml, 3.33 mmole, 1.83 eq). The pH was maintained at 8.0 by dropwise addition of triethylamine and stirring and workup proceeded as described in Example 6. Crystallization from ethanol gave 2.424 g (73.1%) of white amorphous solid, mp 223°–226°; $R_f$ 0.81(C); 0.82(D). Anal. calcd for $C_{96}H_{136}N_{14}O_{21}$·H$_2$O: C, 62.66; H, 7.56; N, 10.66. Found: C, 62.37; H, 7.71; N, 10.68.

EXAMPLE 26

N-$\epsilon$-t-Butyloxycarbonyl-L-lysyl-L-asparaginyl-L-phenylalanyl-L-phenylalanyl-L-tryptophyl-N-$\epsilon$-t-butyloxycarbonyl-L-lysyl-O-t-butyl-L-threonyl-L-phenylalanyl-O-t-butyl-L-threonyl-O-t-butyl-L-serine methyl ester A solution of the protected decapeptide from Example 25 (2.12g, 1.16 mmole), in DMF (15 ml)-methanol (30 ml) containing 5% Pd on BaSO$_4$ (1.5 g) was hydrogenated at atmospheric pressure and worked up as described for the hydrogenation in Example 2. Crystallization from DMF-water gave 1.32 g (67.2%) of white amorphous solid, mp 210°–213.5°; $[\alpha]_D^{25}$ −9.51° (C, 1.1 DMF); $R_f$ 0.67 (D). Anal. calcd for $C_{88}H_{130}N_{14}O_{19}$·H$_2$O; C, 61.95; H, 7.80; N, 11.49. Found: C, 61.89; H, 7.84; N, 11.40.

EXAMPLE 27

N-[2-(p-Biphenylyl)-2-propyloxycarbonylaminoethyl]-N-(2-t-butyloxycarbonylaminoethyl)glycyl-N$^\epsilon$-t-butyloxycarbonyl-L-lysyl-L-asparaginyl-L-phenylalanyl-L-phenylalanyl-N-$\epsilon$-t-butyloxycarbonyl-L-lysyl-O-t-butyl-L-threonyl-L-phenylalanyl-O-t-butyl-L-threonyl-O-t-butyl-L-serine methyl ester A solution of the decapeptide of Example 26 (476 mg, 0.282 mmole), in DMF (5.6 ml) at 0° was reacted with N-[2-(p-biphenylyl)-2-propyloxycarbonyl]-N-(2-t- butyloxycarbonylaminoethyl)glycine N-hydroxysuccinimide ester, (312 mg, 0.564 mmole, 2 eq). N-Methylmorpholine (31.7 μl, 0.282 mmole, 1 eq) was added, the pH maintained at 8.0 and the reaction worked up as described for Example 16. Purification by high performance liquid chromatography (methanol-chloroform gradient) was followed by precipitation from DMF-water to bove 233 mg (39.0%) of white solid, mp 214°–217°; $R_f$ 0.82 (C); 0.77(D); 0.83(E). Anal. calcd for $C_{113}H_{160}N_{16}O_{24}\cdot 3H_2O$: C, 62.24; H, 7.67; N, 10.28. Found: C, 62.02; H, 7.60; N, 10.44.

EXAMPLE 28

N-[2-(p-Biphenylyl)-2-propyloxycarbonylaminoethyl]-N-(2-t-butyloxycarbonylaminoethyl)glycyl-N$^\epsilon$-t-butyloxycarbonyl-L-lysyl-L-asparaginyl-L-phenylalanyl-L-phenylalanyl-N-$\epsilon$-t-butyloxycarbonyl-L-lysyl-O-t-butyl-L-threonyl-L-phenylalanyl-O-t-butyl-L-threonyl-O-t-butyl-L-serine hydrazide The protected peptide of Example 27 (220 mg, 0.103 mmole), in 4 ml of n-butanol-DMF (1:1) was reacted with hydrazine hydrate (0.499 ml, 10.33 mmole, 100 mmole, 100 eq) and stirred at 25° for 21 hrs. The reaction mixture was evaporated to dryness and crystallized from DMF-isopropanol to give 191 mg (86.8%) of white amorphous solid, mp 215°–220°; $R_f$ 0.78(C); 2.28 (6% MeOH—CHCl$_3$). Anal. calcd for $C_{112}H_{160}N_{18}O_{23}\cdot 3H_2O$: C, 61.69; H, 7.67; N, 11.56. Found: C, 61.36; H, 7.65; N, 12.19.

EXAMPLE 29

Cyclo-[N-(2-t-butyloxycarbonylaminoethyl)glycyl-N$^\epsilon$-t-butyloxycarbonyl-L-lysyl-L-asparaginyl-L-phenylalanyl-L-phenylalanyl-L-tryptophyl-N-$\epsilon$-t-butyloxycarbonyl-L-lysyl-O-t-butyl-L-threonyl-L-phenylalanyl-O-t-butyl-L-threonyl-O-t-butyl-L-seryl]

The protected hydrazide from Example 28 (171 mg, 80.4 μmole) was dissolved in 7.64 ml of 0.05 M HCl in DMF (382 μmole, 4.75 eq) and stood at 25° for 1 hr. It was evaporated to dryness and the residue dissolved in 2 ml of DMF, cooled to −20° and treated with 1.77 M HCl in THF (0.31 ml, 0.548 mmole, 6 eq) followed by isoamylnitrite (19.4 μl, 0.137 mmole, 1.5 eq) Stirring proceeded for 30 min at −20°, cooled to −25° and diluted with precooled DMF (174 ml) [final conc of 1 mg/ml]. Diisopropylethylamine (97.3 μl, 0.548 mmole, 6 eq) added and the pH maintained at 8.0 by dropwise addition of diisopropylethylamine. Stirring proceeded at −20° for 1 hr and 2° for 19 hr. It was evaporated to dryness, triturated with water and precipitated from DMF-water to give 93.2 mg (55%) of white amorphous solid, mp 220°–225°; $R_f$ 0.60 (10% MeOH—CHCl$_3$). Anal. calcd for $C_{96}H_{142}N_{16}O_{21}\cdot 3H_2O$: C, 60.36; H, 7.81; N, 11.73. Found: C, 60.57; H, 7.62; N, 11.62.

EXAMPLE 30

Cyclo [Aminoethylglycyl-L-lysyl-L-asparaginyl-L-phenylalanyl-L-phenylalanyl-L-tryptophyl-L-lysyl-L-threonyl-L-phenylalanyl-L-threonyl-L-seryl]

The protected cyclic peptide of Example 29 (40 mg, 21.6 μmole) was reacted with trifluoroacetic acid (10 ml) under N$_2$ at 25° for 2 hr, evaporated to dryness, reevaporated several times from CH$_2$Cl$_2$ and lyophilized from water. It was purified by gel filtration on a 2.5 × 90 cm Sephadex G-15 column using 2.0 N acetic acid-0.01 M β-mercaptoethanol as eluant. Fractions 42–60 (189–270 ml) were lyophilized and further purified by gel filtration on a 1.7 × 74 cm Sephadex G-25 column as above. Fractions 33–41 (79–98 ml) were lyophilized to give 9.2 mg (30.7%); $R_f$ 0.67(C); 0.27(D); 0.80(E).

EXAMPLE 31

Aminoethylglycyl-L-cysteinyl-L-lysyl-L-asparaginyl-L-phenylalanyl-L-phenylalanyl-D-tryptophyl-L-lysyl-L-threonyl-L-phenylalanyl-L-threonyl-Lseryl-L-cysteine By the Solid Phase Procedure. N-t-Butyloxycarbonyl-S-p-methoxybenzyl-L-cysteine was coupled to the hydroxymethyl resin using dicyclohexylcarbodiimide. Deprotection with 25% trifluoroacetic acid (TFA) in CH$_2$Cl$_2$ produced TFA.L-Cys(PMB)-Resin (substitution, 0.260 mm/g). A 2.98 g portion of this resin (0.773 mmole) was treated by the solid phase procedure outlined in the Methods Section and coupled respectively with 4.0 eq of Boc-L-Ser(Bzl)-OH, Boc-L-Thr(Bzl)-OH, Boc-L-Phe-OH, Boc-L-Lys(2-ClZ)-OH, Boc-D-Trp-OH, Boc-L-Phe-OH, Boc-L-Phe-OH, Boc-L-Asn-ONP, Boc-L-Lys(2-ClZ)-OH, Boc-L-Cys(PMB)-OH and Boc-Aeg(Boc)-OH. The couplings were mediated with 4.0 eq of dicyclohexlcarbodiimide for 2 hr (with the exception of Boc-L-Asn-ONP which coupled directly for 24 hr). The peptide-resin (4.73 g) was cleaved at 0° for 45 min with HF (∼50 ml) containing anisole (4.26 ml, 38.7 mmoles). The HF was removed in vacuo and the residue washed with ether, extracted into 0.1M acetic acid (containing 2-mercaptoethanol) and lyophilized to give 0.773 g. A portion (206 mg) was purified by gel filtration on a 2.5 × 90 cm Sephadex G-15 column. Elution proceeded with 2.0M acetic acid-0.01M 2-mercaptoethanol and fractions 42–56 (189–252 ml) were lyophilized. Rechromatography on a 1.7 × 74 cm Sephadex G-25 column gave a major symmetrical peak. Fractions 34–42 (82–101 ml) were lyophilized to give 32.3 mg of white amorphous powder; $R_f$ 0.58(C); 0.72(E); 0.35(D). Amino acid anal: Lys, 2.15, Asp, 1.02; Phe, 2.82; Thr, 1.93; Ser, 0.83; Aeg, 1.08.

EXAMPLE 32

Aminoethylglycyl-L-cysteinyl-L-lysyl-L-asparaginyl-L-phenylalanyl-L-phenylalanyl-L-phenylalanyl-D-tryptophyl-L-lysyl-L-threonyl-L-phenylalanyl-L-threonyl-L-seryl-L-cysteine (oxidized form)

The reduced form of the peptide of Example 31 (15.0 mg, 9.31 μmole), was dissolved in 0.93 ml of 25% acetic acid and treated with potassium ferricyanide and worked up as described in Example 22. The product was purified by gel filtration on a 1.7 × 74 cm Sephadex G-25 column. Fractions 32–45 (70–99 ml) gave a white powder, 6.7 mg (44.7%); $R_f$ 0.55(C); 0.68(E); 0.27(D). Complete disappearance of free sulfhydryls was confirmed by monitoring with Ellman's reagent.

EXAMPLE 33

Aminoethylglycyl-aminoethylglycyl-L-cysteinyl-L-lysyl-L-asparaginyl-L-phenylalanyl-L-phenylalanyl-D-tryptopyl-L-lysyl-L-threonyl-L-phenylalanyl-L-threonyl-L-seryl-L-cysteine By the Solid Phase Procedure: A 2.98 g (.773 mmol) portion of the TFA.L-Cys (PMB)-Resin (substitution 0.260 mm/g) described in Example 31 was treated by the solid phase procedure. Couplings were carried out respectively with 4.0 eq of Boc-L-Ser(Bzl)-OH, Boc-L-Thr(Bzl)-OH, Boc-L-Phe-OH, Boc-L-Lys(2-ClZ)-OH, Boc-D-Trp-OH, Boc-L-Phe-OH, Boc-L-Phe-OH, Boc-L-Asn-ONP, Boc-L-Lys(2-ClZ)-OH, Boc-L-Cys(PMB)-OH, Boc-Aeg(Z)-OH, and Boc-Aeg(Boc)-OH as described in Example 31. The peptide-resin was cleaved at 0° for 1 hr with HF ( 45 ml) containing anisole (4.2 ml, 38.9 mmole). The HF was removed in vacuo and worked up as described in Example 31 to give 915 mg of crude product. A portion (250 mg) was purified by gel filtration on a 2.5 × 90 cm Sephadex G-15 column. Fractions 45-52 (189-234 ml) were lyophilized (56 mg) and rechromatographed on a 1.7 × 74 cm Sephadex G-25 column. Fractions 17-22 (76-99 ml) were lyophilized to give 34 mg of product. Final purification by gel filtration on a 1.7 × 74 cm Sephadex G-25 column [fractions 27-40 (75-100 ml)] gave 29.5 mg of white amorphous powder; $R_f$ 0.50(C); 0.21(D); 0.76(E). Amino acid anal: Lys, 2.15; Asp, 0.99; Phe, 2.84; Thr, 2.08; Ser, 0.86; Aeg, 2.07.

EXAMPLE 34

L-Cysteinyl-L-lysyl-L-asparaginyl-L-phenylalanyl-L-phenylalanyl-L-tryptophyl-L-lysyl-L-threonyl-L-phenylalanyl-L-threonyl-L seryl-L-cysteinyl-aminoethylglycine By the Solid Phase Procedure:

N-Benzyloxycarbonyl-N-(2-t-butyloxycarbonylaminoethyl)-glycine was coupled to the hydroxymethyl resin using dicyclohexylcarbodiimide. Deprotection with 25% TFA in $CH_2Cl_2$ produced TFA·Aeg(Z)-Resin (substitution, 0.259 mm/g). A 2.83 g portion of this resin (0.734 mmol) was treated by the solid phase procedure using the in situ symmetrical anhydride method outlined in the Section and coupled respectively with 5.71 eq of [Boc-L-Cys(PMB)]$_2$O. [Boc-L-Ser(Bzl)]$_2$O, [Boc-L-Thr(Bzl)]$_2$O, [Boc-L-Phe]$_2$O, [Boc-L-Thr(Bzl)]$_2$O, [Boc-L-Lys(2-ClZ)]$_2$O, [Boc-L-Trp]$_2$O, [Boc-L-Phe]$_2$O, [Boc-L-Phe]$_2$O, Boc-L-Asn-ONP, [Boc-L-Lys(2-ClZ)]$_2$O and [Boc-L-Cys(PMB)]$_2$O. The peptide-resin (4.4 g) was cleaved at 0° for 45 min with HF (~45 ml) containing anisol (4.01 ml, 36.4 mmole). The HF was removed in vacuo and worked up as described in Example 31 to give 1.09 g of crude product. A portion (376 mg) was purified by gel filtration on a 2.5 × 90 cm Sephadex G-15 column. Fractions 50-56 (225-252 ml) were lyophilized and rechromatographed on a 1.7 × 74 cm Sephadex G-25 column. Fractions 37-42 (89-101 ml) were lyophilized to give 26 mg of product. Final purification by gel filtration on a 1.7 × 74 cm Sephadex G-25 column [fractions 31-39 (74-94 ml)] gave 17.8 mg of white amorphous powder; $R_f$ 0.59(C); 0.26(D); 0.77(E). Amino acid anal: Lys, 2.09; Asp, 0.92; Phe, 2.78; Thr, 2.03; Ser. 0.82; Aeg, 1.27.

EXAMPLE 35

L-Cysteinyl-L-lysyl-L-asparaginyl-L-phenylalanyl-L-phenylalanyl-D-tryptophyl-L-lysyl-L-threonyl-L-phenylalanyl-L-threonyl-L-seryl-L-cysteinyl-aminoethylglycine By the Solid Phase Procedure: A 2.83 g (.734 mmol) portion of the TFA·Aeg(Z)-Resin (substitution, 0.259 mm/g) described in Example 34 was treated by the solid phase procedure using the in situ symmetrical anhydride method. Couplings were carried out respectively with 5.71 eq of [Boc-L-Cys(PMB)]$_2$O, [Boc-L-Ser(Bzl))]$_2$O, [Boc-L-Thr (Bzl)]$_2$O, [Boc-L-Phe]$_2$O, [Boc-L-Thr(Bzl)]$_2$O, [Boc-L-Lys (2-ClZ)]$_2$O, [Boc-D-Trp]$_2$O, [Boc-L-Phe]$_2$O, [Boc-L-Phe]$_2$O, Boc-L-Asn-ONP, [Boc-L-Lys(2-ClZ)]$_2$O, and [Boc-L-Cys(PMB)-]$_2$O. The peptide-resin (4.47 g) was cleaved at 0° for 1 hr with HF (~45 ml) containing anisole (3.95 ml, 36.6 mmole). The HF was removed in vacuo and worked up as described in Example 31 to give 0.906 g of crude product. A portion (338 mg) was purified by gel filtration on a 2.5 × 90 cm Sephadex G-15 column. Fractions 50-56 (225-252 ml) were lyophilized (57.7 mg) and rechromatographed on a 1.7 × 74 cm Sephadex G-25 column. Fractions 33-40 (79-96 ml) were lyophilized to give 34.4 mg of product. Final purification by gel filtration on a 1.6 × 85 cm Sephadex G-25 column [fractions 46-54 (101-129 ml)] gave 21.8 mg of white amorphous powder; $R_f$ 0.51(C); 0.26(D); 0.82(E). Amino acid anal: Lys, 2.39; Asp. 1.00; Phe, 2.96; Thr, 2.13; Ser. 0.75; Aeg, 1.77.

EXAMPLE 36

Aminoethylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteinyl-aminoethylglycine By the Solid Phase Procedure.

A 2.83 g (0.734 mmol) portion of the TFA·Aeg(Z)-Resin (substitution, 0.259 mm/g) described in Example 34 was treated by the solid phase procedure using the in situ symmetrical anhydride method. Couplings were carried out respectively with 5.71 eq of [Boc-L-Cys(PMB)]$_2$O, [Boc-L-Ser(Bzl)]$_2$O, [Boc-L-Thr(Bzl)]$_2$O, [Boc-L-Phe]$_2$O, [Boc-L-Thr(Bzl)]$_2$O, [Boc-L-Lys(2-ClZ)]$_2$O, [Boc-L-Trp]$_2$O, [Boc-L-Phe]$_2$O, [Boc-L-Phe]$_2$O, Boc-L-Asn-ONP, [Boc-L-Lys(2-ClZ)]$_2$O, [Boc-L-Cys(PMB)]$_2$O and [Boc-Aeg(-Boc)]$_2$O. The peptide-resin (4.54 g) was cleaved at 0° for 45 min with HF (~45) ml) containing anisole (4.01 ml, 37.1 mmole). The HF was removed in vacuo and worked up as described in Example 31 to give 1.22 g of crude product. A portion (963 mg) was purified by gel filtration on a 2.5 × 90 cm Sephadex G-15 column. Fractions 58-71 (261-320 ml) were lyophilized and rechromatographed on the same column. Fractions 44-55 (198-248 ml) were lyophilized to give 72.1 mg of product. Final purification by gel filtration on a 1.7 × 74 cm Sephadex G-25 column [fractions 34-42 (82-101 ml)] gave 43.1 mg of white amorphous product; $R_f$ 0.58 (C); 0.15(D); 0.71(E). Amino acid anal: Lys, 2.20; Asp, 1.00; Phe, 2.87; Thr, 2.05; Ser, 0.80; Aeg, 2.09.

EXAMPLE 37

Aminoethylglycyl-L-cysteinyl-L-lysyl-L-asparaginyl-L-phenylalanyl-L-phenylalanyl-D-tryptophyl-L-lysyl-L-threonyl-L-phenylalanyl-L-threonyl-L-seryl-L-cysteinyl-aminoethylglycine By the Solid Phase Procedure:

A 2.83 g (0.734 mmole) portion of the TFA·Aeg(Z)-Resin (substitution, 0.259 mm/g) described in Example 34 was treated by the solid phase procedure using the in situ symmetrical anhydride method. Couplings were carried out respectively with 5.71 eq of [Boc-L-Cys(PMB)]$_2$O, [Boc-L-Ser(Bzl)]$_2$O, [Boc-L-Thr(Bzl)]$_2$O, [Boc-L-Phe]$_2$O, [Boc-L-Thr(Bzl)]$_2$O, [Boc-L-Lys(2-CiZ)]$_2$O, [Boc-D-Trp]$_2$O, [Boc-L-Phe]$_2$O, [Boc-L-Phe]$_2$O, Boc-L-Asn-ONP, [Boc-L-Lys(2-Clz)]$_2$O, [Boc-L-Cys(PMB)]$_2$O, and [Boc-Aeg(-Boc)]$_2$O. The peptide-resin (4.60 g) was cleaved at 0° for 1 hr with HF (~45 ml) containing anisole (3.95 ml, 36.6 mmole). The HF was removed in vacuo and worked up as described in Example 31 to give 1.09 g of crude product. A portion (240 mg) was purified by gel filtration on a 2.5 × 90 cm Sephadex G-15 column. Fractions (46–55 (207–248 ml) were lyophilized (77.6 mg) and rechromatographed on a 1.6 × 85 cm Sephadex G-25 column. Fractions 44–56 (106–135 ml) were lyophilized to give 51.4 mg of product. Final purification by gel filtration on a 1.6 × 85 cm Sephadex G-25 column [fractions 45–56 (108–135 ml)] gave 25.4 mg of white amorphous product, $R_f$ 0.56(C); 0.21(D); 0.72(E). Amino acid anal: Lys, 2.16; Asp, 0.99; Thr, 2.16; Ser. 0,75; Phe, 2.92; Aeg, 2.00.

EXAMPLE 38

N-t-Butyloxycarbonyl-N-(2-t-butyloxycarbonylaminoethyl)glycine, Boc-Aeg (Boc)-OH A mixture of N-(2-aminoethyl) glycine (7.5 g, 63.5 mmol), magnesium oxide (6.8 g, 169 mmol) and t-butyloxycarbonyl azide (27.0 ml, 191 mmol) in dioxane (63 ml): water (63 ml) was stirred at 50° for 25 hr. It was evaporated to dryness, taken up in water (100 ml), filtered, and extracted with ether (3 × 50 ml). The aqueous layer was acidified (pH 3.5) with citric acid and extracted with ethyl acetate (3 × 50 ml). The ethyl acetate layer was washed with saturated NaCl, dried (MgSO$_4$), filtered, and evaporated to dryness. The residue was crystallized twice from ether-petroleum ether to give 13.23 g (65.5%) of white crystalline product, mp 89°–93.5°; Rf 0.88 (n-BuOH: AcOH: EtOAc: H$_2$O; 1-1-1-1).

Anal. Calcd for $C_{14}H_{26}N_2O_6$:C, 52.86; H, 8.23; N, 8.80. Found: C, 53.09; H, 8.25; N, 8.60.

EXAMPLE 39

N-t-Butyloxycarbonyl-N-(2-t-butyloxycarbonylaminoethyl)glycine N-hydroxy-succinimide ester, Boc-Aeg(Boc)-OSu A solution of Boc-Aeg(Boc)-OH (14.1 g, 44.3 mmol) in CH$_2$Cl$_2$ (250 ml) and DMF (15 ml) was cooled to 0° and treated with N-hydroxysuccinimide (5.61 g, 48.7 mmol) and dicyclohexylcarbodiimide (10.1 g, 48.7 mmol). Reaction proceeded at 0° for 1 hr. and 25° for 16 hr. It was filtered, extracted with NaHCO$_3$, saturated NaCl, 1M critric acid, saturated NaCl, dried over MgSO$_4$, filtered and evaporated to dryness. Crystallization from ethyl acetate-petroleum ether gave white crystalline product, 17.0 g (92.4%); mp 132°–136°.

Anal. Calcd. for $C_{18}H_{29}N_3O_8$: C, 52.04; H, 7.04; N, 10.11 Found: C, 52.17; H, 6.86; N, 10.08.

EXAMPLE 40

N-(2-Benzyloxycarbonylaminoethyl)glycine; Z-Aeg-OH

A solution of benzyl p-nitrophenylcarbonate (165.1 g, 0.605 mol) in dioxane (1.31) was added dropwise to a stirring solution of N-(2-aminoethyl) glycine (47.58 g, 0.4032 mol) in water (1.3 l) and dioxane (1.3 l) and maintained at pH 11 by addition of 2N NaOH. Reaction proceeded at 25° for 16 hr. It was evaporated to dryness, taken up in water (1.2 l) and filtered. The filtrate was extracted with ethyl acetate (2 × 1.3 l) and the aqueous layer acidified with 6N HCl to pH 5.5 and extracted with ether (2 × 1.4 l). The aqueous layer was acidified to pH 1, evaporated to dryness and reevaporated from isopropanol. The residue was crystallized from isopropanol to give 50.7 g (44%) of white crystals; mp 176°–177°.

Anal. Calcd. for $C_{12}H_{16}N_2O_4$·HCl C, 49.92; H, 5.93; N, 9.83; Cl 12.28 Found: C, 49.81; H, 6.07; N, 9.70; Cl 12.13.

EXAMPLE 41

N-t-Butyloxycarbonyl-N-(2-benzyloxycarbonylaminoethyl)glycine; Z-Aeg (Boc)-OH A mixture of Z-Aeg-OH (940 mg, 3.7 mmol), magnesium oxide (700 mg, 7.4 mmol) and t-butyloxycarbonylazide (1.02 ml, 7.4 mmol) in dioxane (10 ml): water (10 ml) was stirred at 50° for 24 hr. It was evaporated to dryness, taken up in water (50 ml), filtered, and extracted with ether (3 × 50 ml). The aqueous layer was acidified (pH 3.5) with citric acid and extracted with ethyl acetate (3 × 50 ml). The ethyl acetate layer was washed with saturated NaCl, dried (MgSO$_4$), filtered, and evaporated to dryness. The residue was crystallized from ethylacetate-petroleum ether to give 952 mg (72.7%) of white crystalline product mp 118°–119.5°; Rf 0.70 (n-BuOH: AcOH: pyr: H$_2$O; 15-3-10-12); Rf 0.76 [n-BuOH: AcOH: H$_2$O; 4-1-5 (upper phase)].

Anal. Calcd. for $C_{17}H_{24}N_2O_6$: C, 57.94; H, 6.86; N, 7.95. Found: C, 58.00; H, 6.84; N, 7.86.

EXAMPLE 42

N-t-Butyloxycarbonyl-N-(2-aminoethyl)glycine; H-Aeg (Boc)-OH

A solution of Z-Aeg (Boc)-OH (0.90 g, 2.55 μmol) in methanol (25 ml) containing 0.7 g of 5% Pd-BaSO$_4$ was hydrogenated for 2.5 hr. at 25°. It was filtered, evaporated to dryness and crystallized from methanol-ether to give 430 mg (77.1%) of white crystalline product, mp 210°–212°; Rf 0.48 (n-BuOH: AcOH: Pyr: H$_2$O; 15-3-10-12).

Anal. Calcd. for $C_9H_{18}N_2O_4$: C, 49.53; H, 8.31; N, 12.84. Found: C, 49.58; H, 8.23; N, 13.18.

EXAMPLE 43

N-Benzyloxycarbonyl-N-(2-t-butyloxycarbonylaminoethyl)glycine; Boc-Aeg (Z)-OH A solution of N-(2-aminoethyl)glycine (8.85 g, 75 mmol) in water (112 ml) and dioxane (112 ml) was adjusted to pH 11.2 with 2N NaOH. A solution of t-butyl p-nitrophenylcarbonate (26.9 g, 112.5 mmol) in dioxane (112 ml) was added dropwise and stirring proceeded at pH 11 for 16 hr. at 25°. It was evaporated to dryness, taken up in water (300 ml), filtered, and extracted with ether (3 × 200 ml). The aqueous layer was acidified with 2N HCl to pH 5.5 and extracted with ether (3 × 200 ml). The aqueous layer was readjusted to pH 9.7 with 2N NaOH and treated with benzyl chloroformate (11.4 ml, 85 mmol). Stirring proceeded at 25° for 16 hr. at pH 9.5. It was extracted with ether (3 × 200 ml). The aqueous layer was acidified with 2N HCl to pH 1.5 and extracted with ethyl acetate (3 × 200 ml), dried (Na$_2$SO$_4$), filtered and evaporated to dryness. Crystallization from ether-petroleum ether gave 9.4 g (35.6%) of white crystal; mp 90–95° ; Rf 0.4(CHCl$_3$: MeOH; 80-20). Lit. mp 90–91° (E. Atherton, et al., J. Chem. Soc. (C), 3393 (1971).

EXAMPLE 44

N-t-Butyloxycarbonyl-N-(2-t-butyloxycarbonylamino-ethyl)glycyl-N-(2-t-butyloxycarbonylaminoethyl)glycine; Boc-Aeg(Boc)-Aeg(Boc)-OH A solution of Boc-Aeg(Boc)-OSu (727 mg, 1.75 mmol) and H-Aeg(Boc)-OH (382 mg, 1.75 mmol) in DMF (15 ml) was treated with N-methylmorpholine (0.20 ml, 1.75 mmol) and stirred at 25° for 16 hr. Additional N-methylmorpholine was added to maintain pH 7.5–8. It was evaporated to dryness, taken up in ethyl acetate, extracted with 0.1 M citric acid (2 × 25 ml), saturated NaCl, dried (MgSO$_4$), filtered, evaporated to dryness and triturated with pentane to give white amorphous powder, 873 mg (96.3%); Rf 0.70 (n-BuOH: AcOH: Pyr: H$_2$O; 15-3-10-12).

Anal. Calcd. for $C_{23}H_{42}N_4O_9$: C, 53.27; H, 8.16; N, 10.80 Found: C, 53.13; H, 8.41; N, 10.65.

EXAMPLE 45

N-t-Butyloxycarbonyl-N-(2-t-butyloxycarbonylamino-ethyl)glycyl-N-(2-t-butyloxycarbonylaminoethyl)glycine N-hydroxysuccinimide ester; Boc-Aeg(Boc)-Aeg(Boc)-OSu A solution of Boc-Aeg(Boc)-Aeg(Boc)-OH (778 mg, 1.50 mmol) in CH$_2$Cl$_2$ (12 ml) and DMF (1 ml) was cooled to 0° and treated with N-hydroxysuccinimide (196 mg, 1.7 mmol) and dicyclohexylcarbodiimide (351 mg, 1.7 mmol). Reaction proceeded at 0° for 1 hour and 25° for 16 hours. It was filtered, evaporated to dryness and crystallized from ethyl acetate- petroleum ether to give 689 mg (74.6%) of white crystalline product, mp 90–94°. Anal. calcd. for $C_{27}H_{45}N_5O_{11}$; C, 52.67; H, 7.38; N, 11.38. Found; C, 53.11; H, 7.54; N, 11.34.

EXAMPLE 46

N-t-Butyloxycarbonyl-N-(2-t-butyloxycarbonylamino-ethyl)glycyl-L-alanine; Boc-Aeg(Boc)-Ala-OH A solution of Boc-Aeg(Boc)-OSu (1.039 g, 2.5 mmol) and L-alanine (223 mg, 2.5 mmol) in DMF (5 ml) was treated with N-methylmorpholine (0.35 ml, 2.5 mmol) and stirred at 25° for 48 hours. Additiional N-methylmorpholine was added to maintain pH 7.5 – 8. It was evaporated to dryness, taken up in ethyl acetate, extracted with 0.5 M citric acid (2 × 25 ml), saturated NaCl, dried (MgSO$_4$), filtered, evaporated to dryness and crystallized from ether-petroleum ether to give 567 mg (58.2%); mp 106–113°; R$_f$9.70 (n-BuOH: Pyr: H$_2$O; 15-3-10-12). Anal. calcd. for $C_{17}H_{31}N_3O_7$; C, 52.43; H, 8.02; N, 10.79. Found C, 52.20; H, 8.12; N, 10.70.

EXAMPLE 47

N-t-Butyloxycarbonyl-N-(2-butyloxycarbonylaminoe-thyl)glycyl-L-alanyl-glycine N-hydroxysuccinimide' ester A solution of Boc-Aeg(Boc)-Ala-OH (200 mg, 0.514 mmol) in THF (2 ml) was cooled to $-15°$ and treated with N-methylmorpholine (58 µl, 0.514 mmol) followed by isobutyl chloroformate (68 µl, 0.514 mmol). After stirring at $-15°$ for 1 minute, the reaction mixture was cooled to $-20°$ and TFA×H-Gly-OSu (147 mg, 0.514 mmol) in THF (0.5 ml) added. N-Methylmorpholine 58 µl 0.514 mmol) was added and stirring proceeded at $-15°$ for 1 hour and 25° for 4 hours. It was evaporated to dryness, taken up in ethyl acetate, extracted with 5% NaHCO$_3$, saturated NaCl, 1 M citric acid, dried (MgSO$_4$), filtered, evaporated to dryness and dried in vacuo. White amorphous solid, 208 mg (74.4%) was obtained. Anal. calcd. for $C_{23}H_{37}N_5O_{10}$. ½ H$_2$O; C, 50.01; H, 6.93; N, 12.67. Found; C, 50.32; H, 6.88; N, 12.10.

EXAMPLE 48

Aminoethylglycyl-aminoethylglycyl-L-cysteinyl-L-lysyl-L-asparaginyl-L-phenylalanyl-L-phenylalanyl-D-tryptophyl-L-lysyl-L-threonyl-L-phenylalanyl-L-threonyl-L-seryl-L-cysteine(oxidized form)

The reduced form of the peptide, aminoethylglycyl-aminoethylglycyl-L-cysteinyl-L-lysyl-L-asparaginyl-L-phenylalanyl-L-phenylalanyl-D-tryptophyl-L-lysyl-L-threonyl-L-phenylalanyl-L-threonyl-L-seryl-L-cysteine,(20 mg, 11.7µmol)was dissolved in 1.1 ml of 25% acetic acid, diluted with 34 ml H$_2$O and treated with potassium ferricyanide and worked up as described in Example 22. The product was purified by gel filtration on a 1.7 × 74 cm Sephadex G-25 column. Fractions 26–37 (64–91 ml) gave a white powder, 12.4 mg (62%); Rf 0.51 (C); 0.22 (D); 0.68 (E). Complete disappearance of free sulfhydryls was confirmed by monitoring with Ellman's reagent.

EXAMPLE 49

A. Gastric Antisecretory Activity of Somatostatin Analogs

The gastric antisecretory effect of somatostatin analogs was studied in a model which utilizes unanesthetized rats. The test compounds are shown in the following table.

SOMATOSTATIN ANALOGS CONTAINING AMINOETHYLGLYCINE (Aeg)

| Compound | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| A | H—Ala | —Gly | —Cys | —Lys | —Asn | —Phe | —Phe | —Trp | —Lys | —Thr | —Phe | —Thr | —Ser | —Cys—OH |
| B | H—Ala | —Gly | —Cys | —Lys | —Asn | —Phe | —Phe | —Trp | —Lys | —Thr | —Phe | —Thr | —Ser | —Cys—OH |
| C | | | H—Cys | —Lys | —Asn | —Phe | —Phe | —Trp | —Lys | —Thr | —Phe | —Thr | —Ser | —Cys—OH |
| D | | | | —Lys | —Asn | —Phe | —Phe | —Trp | —Lys | —Thr | —Phe | —Thr | —Ser | (cyclic: —C(=O)—CH$_2$—NH—CH$_2$—CH$_2$—NH—) |
| E | H—Aeg | —Ala | —Gly | —Cys | —Lys | —Asn | —Phe | —Phe | —Trp | —Lys | —Thr | —Phe | —Thr | —Ser—Cys—OH |
| F | | H—Aeg | —Cys | —Lys | —Asn | —Phe | —Phe | —Trp | —Lys | —Thr | —Phe | —Thr | —Ser | —Cys—OH |
| G | | H—Aeg | —Cys | —Lys | —Asn | —Phe | —Phe | —Trp | —Lys | —Thr | —Phe | —Thr | —Ser | —Cys—OH |
| H | H—Aeg | —Aeg | —Cys | —Lys | —Asn | —Phe | —Phe | —Trp | —Lys | —Thr | —Phe | —Thr | —Ser | —Cys—OH |
| I | | | H—Cys | —Lys | —Asn | —Phe | —Phe | —Trp | —Lys | —Thr | —Phe | —Thr | —Ser | —Cys—Aeg—OH |
| J | | H—Aeg | —Cys | —Lys | —Asn | —Phe | —Phe | —Trp | —Lys | —Thr | —Phe | —Thr | —Ser | —Cys—Aeg—OH |
| K | H—Ala | —Gly | —Cys | —Lys | —Asn | —Phe | —Phe | —D-Trp | —Lys | —Thr | —Phe | —Thr | —Ser | —Cys—OH |

| Compound | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| L | | H—Aeg | Cys | Lys | Asn | Phe | Phe | D-Trp | Lys | Thr | Phe | Thr | Ser | Cys—OH |
| M | | H—Aeg | Cys⎯ | Lys | Asn | Phe | Phe | D-Trp | Lys | Thr | Phe | Thr | Ser | ⎯Cys—OH |
| N | H—Aeg | Aeg | Cys | Lys | Asn | Phe | Phe | D-Trp | Lys | Thr | Phe | Thr | Ser | Cys—OH |
| O | H—Aeg | Aeg | Cys⎯ | Lys | Asn | Phe | Phe | D-Trp | Lys | Thr | Phe | Thr | Ser | ⎯Cys—OH |
| P | | H—Cys | Lys | Asn | Phe | Phe | D-Trp | Lys | Thr | Phe | Thr | Ser | Cys | Aeg—OH |
| Q | H—Aeg | Cys | Lys | Asn | Phe | Phe | D-Trp | Lys | Thr | Phe | Thr | Ser | Cys | Aeg—OH |

(In Compounds M and O, the two Cys residues are joined by a disulfide bridge.)

The essential features of this model are as follows.

All operative techniques were carried out on fasted female albino rats (average weight 250 g), under Penthrane anesthesia, using montraumatic microsurgical instruments, polyethylene tubing and a special adhesive. The basic model used in the present studies consisted of:

(a) Catheterization of the inferior vena cava. This allowed adequate hydration through the constant infusion of 0.15M NaCl (at the rate of 1.4 ml/hr.). This catheter was also used for i.v. administration of solutions of the test compounds.

(b) Catheterization of the stomach. A cannula in the forestomach allowed washing of the gastric lumen with saline (before experiments). Water (0.2 ml/10 min) was infused through this catheter during the experimental periods. This was done to prevent obstruction of the "collecting" cannula (see below) by gastric debris and to obtain a practical workable volume to measure several parameters of gastric secretion. A second cannula was positioned in the glandular stomach, close to the greater curvature, in the more dependent site and in such a way as to allow collection, by gravity, of all fluids emerging from the stomach. Passage of these secretions through a small glass container permitted continuous recording of pH by means of a glass microelectrode. A fraction collector was used to simultaneously obtain the gastric secretions.

(c) Catheterization of the lower part of the common bile duct to procure mixed secretions of bile and pancreatic juice as a function of time. This was done with the purpose of examining the effect of these compounds, if any, on bile flow.

This preparation is suitable for the bioassay of microgram quantities of gastric secretory depressants in which each animal serves as its own control. The rats (250 g b.w.) were allowed to attain a period of stabilized gastric acid output (for one hour) and were then injected intravenously (100 μl) with 200 μg of the test compound. This single bolus injection was immediately followed by a rinsing injection of 50 μl saline, thus insuring quantitative delivery of the dose. The pH was recorded continuously for 1 hour before and 1 ½ hour after the i.v. injection of the test compounds. The gastric secretions were collected over 10-minute intervals before and after dosage. Four parameters of gastric secretion were evaluated: (a) changes in the negative logarithm of the hydrogen ion activity (pH, determined by the glass electrode either by a continuous trace or in samples taken at 10-minute intervals); (b) volume; (c) total acid concentration (μEq/ml); and d) total acid output (μEq/10-min periods). The results, can be summarized as follows:

1. pH and Acid Concentration (a) The reduced form of somatostatin (Compound B) is as active as the oxidized, cyclic somatostatin (Compound A).

(b) Deletion of the N-terminal dipeptide (des-Ala$^1$-Gly$^2$-) as in Compound C or elongation by addition of Aeg to the N-terminus as in Compound E, severely decreases activity. Compound C actually stimulated gastric acid secretion. Elongation by attachment of Aeg to the C-terminal, as in Compound I and Compound J, results in compounds which are less active than somatostatin.

(c) The novel carba-somatostatin analog which contains Aeg in the ring portion (Compound D) exhibits erratic activity.

(d) Replacement of the N-terminal dipeptide Ala$^1$-Gly$^2$-for either Aeg (as in Compound F and Compound G) or Aeg-Aeg (as in Compound H) produces compounds with increased activity and longer duration of effect.

(e) Insertion of a D-Trp in position 8, instead of the L-form, as in Compound K, reduces activity.

(f) Marked increase in biological activity and signaificantly longer duration of effect is observed by the combination of more than one substitution in the somatostatin molecule, as in Compound L and its oxidized form, Compound M.

2. Volume and Acid Output

With a few exceptions, those compounds which were more active than somatostatin in terms of increasing pH and decreasing total gastric acid concentration were also more active in inhibiting the volume as well as the total acid output in the conscious gastric fistula rat. When the four parameters of gastric acid secretion are taken into account, Compound L and Compound M -which incorporate substitution of Ala$^1$-Gly$^2$-by Aeg as well as L-Trp$^8$ by the D-form - appear to be the most active compounds of this series.

B. Stimulation of Mucoprotein Production

Stimulation of mucus production is thought to be a desirable biological property of compounds with potential clinical application in the treatment of peptic ulcer disease. For this reason, initial studies were carried out to explore the possibility that analogs such as Compound M, which are more active than somatostatin, may have an effect on gastric mucus production.

Overnight fasted rats received saline solutions of either Compound M or Compound A at the antisecretory dose of 800μg/kg administered intraperitoneally. Control rats were given only vehicle. All animals were sacrificed by decapitation 1 hour after dosing. After opening the abdomen the stomach was removed and its contents were washed away with 10 ml of a 0.85%

NaCl solution. The excised stomachs were cut open along the greater curvature and the exposed gastric mucosa was carefully scraped. The scrapings were homogenized in 5 ml of the 0.85% NaCl solution and subjected to chemical analysis. Total hexoses were determined by the anthrone reaction, which is based on the formation in concentrated sulfuric acid of furfural derivatives which react with anthrone to form a blue-green color; this reaction has the advantage of being applied directly to the glycoprotein with color formation occuring concurrently with the liberation of sugars (Methods in Enzymology, Vol. VIII, pp. 4–5 1966). Fucose in the unhydrolyzed mucoprotein was determined by the Dische-Shettes cysteine-sulfuric acid reaction for methyl pentoses. This method allows accurate determination of fucose even in the presence of large amounts of hexoses and peptide material (Methods in Eznymology, Vol. VIII, pp 11–13 , 1966).

Total protein was determined using the Lowry method.

The results have been summarized in Table 1. One hour after treatment, scraping of gastric mucosa from animals treated with Compound M contained higher concentrations of carbohydrates (hexoses and fucose) as well as total protein than the control group. Dosage with Compound A produced an increment of the total protein, but it did not appear to influence concentration of carbohydrates. Compound M appeared to be somewhat more active than Compound A, but this difference did not reach statistical significance.

of the untreated animals after 9 hours of immobilization. In cats, somatostatin, administered by continuous intravenous infusion in graded doses (range: 0.62 to 5.0 $\mu$g/kg-hr) effectively prevented the formation of duodenal ulcers produced by prolonged administration of both pentagastrin or histamine (Konturek, et al., Scand, J. Gastroent. 12: 379–383, 1977). Also pertinent is the work of Mattes, et al. (Horm. Metab. Res. 7: 508–511, 1975) who reported their results of an extended somatostatin treatment in a 65 year-old male patient with heavy gastrointestinal bleeding on the 9th postoperative day following a high Billroth I-resection. Endoscopy revealed the bleeding to be caused by two residual ulcers in the area of the anastomosis. A dose of 250 $\mu$g of synthetic cylic somatostatin was administered i.v. as a bolus. This was followed by an infusion of 250 $\mu$g per hour for 67 hours. Somatostatin treatment led to an immediate cessation of the bleeding after 1 hour. Endoscopy at the end of treatment period showed two ulcers in the process of healing.

Since the above reports suggest that somatostatin may possess antiulcerogenic activities, it was of interest to explore the effects of some of the derivatives of somatostatin containing Aeg. In both studies CD-1 male mice weighing between 18–25 g were used. The mice were fasted for 19 hours prior to the initiation of restraint-immersion which involved restraining animals in rubber hoses and immersion in water (21° C.) to the height of the xiphoid process. In the first study, just prior to the initiation of the restraint-immersion proce- Table 1

THE EFFECT OF INTRAPERITONEALLY ADMINISTERED COMPOUND M OR COMPOUND A ON THE GASTRIC MUCOSAL CONCENTRATIONS OF CARBOHYDRATES AND TOTAL PROTEIN IN THE RAT[a]

| | Carbohydrate ($\mu$g/total sample) | | | | | | Total Protein ($\mu$g/total sample) | | |
|---|---|---|---|---|---|---|---|---|---|
| | Hexose | | | Fucose | | | | | |
| | Control | After Compound A | Compound M | Control | After Compound A | Compound M | Control | After Compound A | Compound M |
| Mean | 152.5[b] | 235.3[c] | 243.5[d] | 21.8[e] | 46.2[f] | 44.8[g] | 63.8[h] | 350.0[i] | 303.2[j] |
| S.E.M. ($\pm$) | 18.5 | 33.8 | 24.5 | 1.6 | 11.4 | 3.9 | 9.5 | 79.7 | 45.4 |

[a]Rats were administered Compound M or Compound A at the antisecretory dose of 800 $\mu$g/kg b.w., in 0.5 ml saline. There were 6 animals per group. The average weight in the control groups was (in grams), 220.3 $\pm$ 3.2. The average weight for the Compound M group and the Compound A group was (in grams), 234.7 ($\pm$ 7.7) and 222.3 ($\pm$ 4.0), respectively.
[b,c,d,e,f,g,h,i,j]Figures in these columns were compared (by means of the Student's t-test) to their corresponding controls (b,e, and h); with the following results:
c vs. b; p > 0.050 (NS)
d vs. b; p < 0.050 (S)
c vs. d; p > 0.050 (NS)
f vs. e; p > 0.050
g vs. e; p < 0.005
f vs. g; p > 0.050
i vs. h; p < 0.020 (S)
j vs. h; p < 0.005 (S)
i vs. j; p > 0.050 (NS)

These data suggest that certain analogs of somatostatin with high antisecretory activity of longer duration of action, such as Compound M, are also capable of provoking an enhancement of mucus production in the stomach wall of the normal rat.

C. Antiulcerogenic Activity

Recently, Zierden and his colleagues (Res. Exp. Med. 168: 199–201, 1976) studied the possible prophylactic effect of somatostatin on stress ulcer formation. The method employed consisted of restraining rats by the standard effectively prevented the formation of of Brodie and Hanson (Gastroenterology 38: 353–360, 1960). Before starting the test as well as 3 h and 6 h later, animals (means body weight = 192 g) received subcutaneous injection of somatostatin (100 $\mu$g linear protamine-zinc-somatostatin/rat). Rats treated with somatostatin before and during stress had only 1/5 of the ulcers dure, mice received, via the subcutaneous route, graded amounts (0.1 to 10 mg/kg b.w.) of somatostatin (Compound A), Compound F, or vehicle (5% acacia); this administration was repeated two hours later. In the second study, the compounds (Compound A, Compound L, or vehicle) were administered only once, just prior to the initiation of the restraint-immersion procedure. Following four hours of restraint-immersion the animals (both studies) were killed and their stomachs examined for ulceration. The degree of ulceration was determined by the amount of visible blood present in the stomach and was rated on a scale of 0 to 4, with 0 being no detectable blood and 4 being a massive amount of blood. All compounds were dispersed in 5% acacia and administered at a dosage volume of 0.2 ml per 20 grams of body weight. The antiulcerogenic ED50 values were calculated using percent protection as the response and a computer program ("ED50") based on the probit method of Finney (Finney, "Probit Analysis", Cambridge University Press, 1971). The comparative effectiveness (relative potency R. P.) of somatostatin and Compound F (first study) or somatostatin and Compound L (second study) was determined from the dose responses using an "ED50" computer program.

In the first study, both somatostatin and the somatostatin anlaog Compound F were found to be effective in preventing restraint-immersion induced gastric ulceration in the mouse; Compound F was ca 5.6-fold less potent that somatostatin. The respective ED50 values for Compound F and somatostatin were 1.93 and 0.35 mg/kg. The second study demonstrated that Compound L was ca. 4.6-fold more potent than somatostatin. This value was based on the computer generated term R. P. (relative potency), an analysis which considers the entire dose response curve. However, on the basis of ED50 values, Compound L was found to be ca. 6.8-fold more potent than somatostatin (see Table 2).

Somatostatin analogs with high and prolonged antisecretory activity, such as Compound L, are also more potent inhibitors of restraint-immersion ulcer formation than somatostatin. These results suggest that certain somatostatin analogs could be useful in the treatment of peptic ulceration.

Table 2

| ANTI-ULCEROGENIC ACTIVITY OF SOMATOSTATIN AND COMPOUND L IN THE MOUSE RESTRAINT-IMMERSION TEST | |
|---|---|
| | ED50 (mg/kg) |
| Somatostatin (Compound A) | 6.70 |
| Compound L | 0.98 |

D. Gastric Antisecretory Activity of Compound N After Intragastric Administration The unanesthetized rat model was used in an exact manner to that employed in the evaluation of gastric antisecretory activity after parenteral administration described above in A, with the following modification. Following recording of the gastric pH for 1 hour, drainage of the gastric secretions was interrupted by means of a forceps. Saline solutions (total volume = 1000 μl) of Compound N (at the dose of 8 mg/kg b.w.) were then intragastrically administered, via the canula in the avascular stomach, which was closed. Fifteen minutes later, the catheter draining the gastric secretions was reopened; the water infusion through the catheter in the forestomach was simultaneously reestablished. The pH was now recorded continuously for 1 ½ hours. Samples of gastric juice were taken before and after treatment, and analyzed for the usual four parameters of gastric secretion.

The results obtained demonstrate that Compound N is active after intragastric administration.

We claim:

1. A compound of the formula

X-Lys-Asn-Phe-Phe-A-Lys-Thr-Phe-Thr-Ser-Y wherein X independently is selected from H-(Aeg)$_m$-Cys- and H-(Aeg)$_m$-Ala-Gly-Cys-; A is L-Trp or D-Trp; Y independently is Cys-(Aeg)$_n$-OH; X and Y taken together are an aminoethylglycyl radical in the ring position; m and n are independently selected from 0,1,2,3 and 4 provided that at least one of X or Y contains at least one Aeg radial; and the cylic disulfide compounds, the protamine zinc and protamine aluminum complexes and the pharmaceutically acceptable acid addition salts thereof.

2. The compound of claim 1 which is

H-Aeg-Cys-Lys-Asn-Phe-Phe-Trp-Lys-Thr-phe-Thr-Ser-Cys-OH.

3. The compound of claim 1 which is

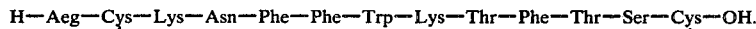

4. The compound of claim 1 which is

H-Aeg-Aeg-Cys-Lys-Phe-Phe-Trp-Lys-Thr-Phe-Thr-Ser-Cys-OH.

5. The compound of claim 1 which is

H-Aeg-Ala-Gly-Cys-Lys-Asn-Phe-Phe-Trp-Lys-Thr-Phe-Thr-Ser-Cys-OH

6. The compound of claim 1 which is

H-Aeg-Cys-Lys-Asn-Phe-Phe-D-Trp-Lys-Thr-Phe-Thr-Ser-Cys-OH.

7. The compound of claim 1 which is

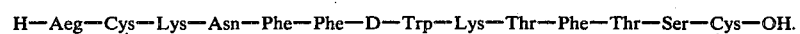

8. The compound of claim 1 which is

H-Aeg-Aeg-Cys-Lys-Asn-Phe-Phe-d-Trp-Lys-Thr-Phe-Thr-Ser-Cys-OH.

9. The compound of claim 1 which is

10. The compund of claim 1 which is

H-Cys-Lys-Asn-Phe-Phe-Trp-Lys-Thr-Phe-Ser-Cys-Aeg-OH.

11. The compound of claim 1 which is

H-Cys-Lys-Asn-Phe-PHe-D-Trp-Lys-Thr-Phe-Thr-Ser-Cys-Aeg-OH.

12. The compound of claim 1 which is

13. The compound of claim 1 which is
H-Aeg-Cys-Lys-Asn-Phe-Phe-Trp-Lys-Thr-Phe-Thr-Ser-Cys-Aeg-OH.

14. The compound of claim 1 which is
H-Aeg-Cys-Lys-Asn-Phe-Phe-D-Trp-Lys-Thr-Ser-Cys-Aeg-OH.

[ Aeg—Lys—Asn—Phe—Phe—Trp—Lys—Thr—Phe—Thr—Ser ]

\* \* \* \* \*